United States Patent
Bickerdike et al.

(10) Patent No.: US 8,519,127 B2
(45) Date of Patent: Aug. 27, 2013

(54) CYCLIC GLYCYL-2-ALLYL PROLINE AND ITS USE IN TREATMENT OF PERIPHERAL NEUROPATHY

(76) Inventors: Mike John Bickerdike, Auckland (NZ); Margaret Anne Brimble, Auckland (NZ); Ernest Stephen Sirimanne, Auckland (NZ)

( * ) Notice: Subject to any disclaimer, the term of this patent is extended or adjusted under 35 U.S.C. 154(b) by 228 days.

(21) Appl. No.: 12/891,280

(22) Filed: Sep. 27, 2010

(65) Prior Publication Data

US 2011/0052531 A1 Mar. 3, 2011

Related U.S. Application Data

(63) Continuation-in-part of application No. 10/570,395, filed as application No. PCT/US2004/028308 on Aug. 31, 2004, now Pat. No. 8,067,425.

(60) Provisional application No. 60/499,956, filed on Sep. 3, 2003, provisional application No. 61/245,748, filed on Sep. 25, 2009, provisional application No. 61/257,296, filed on Nov. 2, 2009.

(51) Int. Cl.
*C07D 241/36* (2006.01)

(52) U.S. Cl.
USPC .......................................... 544/282

(58) Field of Classification Search
USPC .......................................... 544/282
See application file for complete search history.

(56) References Cited

FOREIGN PATENT DOCUMENTS

WO  WO 99/40931  8/1999

OTHER PUBLICATIONS

Office Action dated Mar. 11, 2009 in U.S. Appl. No. 11/399,974.
IDS in U.S. Appl. No. 11/399,974 dated May 5, 2009.
Reply to Office Action dated Jun. 16, 2009 in U.S. Appl. No. 11/399,974.
Office Action dated Sep. 25, 2009 in U.S. Appl. No. 11/399,974.
Mann, et al. "Domapminergic neurotransmitter systems in Alzheimer's disease and in Down's syndrome at middle age," Journal of Neurology, Neurosurgery and Psychiatry 1987.
Zarkovic, "4-Hydrononenal and neurodegenerative diseases," Molecular Aspects of Medicine 24 (2003) 293-303.
Kostic, "Midbrain Dopaminergic Neuronal Degeneration in a Transgenic Mouse Motel of Familial Amyotrophic Lateral Scierosis," American Neurological Assocation 1997, 497-504.
Guttman, Mark, "Currect Concepts in the diagnosis and management of Parkinson's Disease," Canadian Medical Association 2003, 293-301.
Reply to Final Office Action dated Feb. 9, 2011 in U.S. Appl. No. 10/570,395.
Office Action dated Dec. 21, 2010 in U.S. Appl. No. 10/570,395.
Reply to Office Action dated Oct. 12, 2010 in U.S. Appl. No. 10/570,395.
Office Action dated May 10, 2010 in U.S. Appl. No. 10/570,395.
Reply to Office Action dated Apr. 21, 2010 in U.S. Appl. No. 10/570,395.
Office Action dated Feb. 2, 2010 in U.S. Appl. No. 10/570,395.
Reply to Office Action dated Oct. 20, 2009 in U.S. Appl. No. 10/570,395.
Office Action dated May 28, 2009 in U.S. Appl. No. 10/570,395.
Office Action dated Jan. 21, 2010 in U.S. Appl. No. 10/570,395.
Reply to Office Action dated Mar. 13, 2009 in U.S. Appl. No. 10/570,395.
Office Action dated Feb. 2, 2009 in U.S. Appl. No. 10/570,395.
Second Preliminary Amendment dated Dec. 17, 2007 in U.S. Appl. No. 10/570,395.
PCT/US10/002636 Prelim Rt, Sep. 27, 2010, Neuren Pharmaceuticals.
Strategy for the Synthesis of Non-Proteinogenic Dipeptides, Liebigs Ann.Chem. 1988, 1025-1031; VCH Verlagsgesellachaft mbH, D-6940 Weinheim, 1988.
Cerebral Blood Flow & Metabolism, 23:342-354, 2003, The International Society for Cerebral Blood Flow and Metabolism, Lippincott Williams & Wilkins, Inc., Philadelphia.
Prakash, K.R.C., "Synthesis and Biological Activity of Novel Neuroprotective Diketopiperazines," Bioorganic & Medicinal Chemistry 10 (2002) 3043-3048, Elsevier Science Ltd.

*Primary Examiner* — Brian McDowell
(74) *Attorney, Agent, or Firm* — D. Benjamin Borson; Borson Law Group, PC

(57) ABSTRACT

Embodiments of this invention provide methods for therapeutic use of cyclic G-2-allylProline (cG-2-allylP) to treat peripheral neuropathies, including toxin-induced peripheral neuropathy and diabetic peripheral neuropathy as well as manufacture of medicaments including tablets, capsules, and other orally active compositions containing cG-2-allylP, as well as injectable solutions that are useful for treatment of such conditions.

9 Claims, 6 Drawing Sheets

CYCLIC GLYCYL-2-ALLYL PROLINE AND ITS USE IN TREATMENT OF PERIPHERAL NEUROPATHY

CLAIM OF PRIORITY

This application is a Continuation-In-Part of application Ser. No. 10/570,395, filed Mar. 2, 2007, entitled "Neuroprotective Bicyclic Compounds and Methods for Their Use," Margaret Anne Brimble, Juan Guan, and Frank Sieg, inventors, now U.S. Pat. No. 8,067,415, issued Nov. 29, 2011, which claims priority to PCT International Patent Application No. PCT/US2004/28308, filed Aug. 31, 2004, which claims the priority under 35 U.S.C. 119(e) to U.S. Provisional Application No. 60/499,956 filed Sep. 3, 2003, Margaret Anne Brimble, Jian Guan and Frank Sieg, inventors, titled "Neuroprotective Bicyclic Compounds and Methods for Their Use." This application also claims priority to U.S. Provisional Patent Application No. 61/245,748, filed Sep. 25, 2009 and U.S. Provisional Patent Application No. 61/257,296, filed Nov. 2, 2009, each entitled "Cyclic Glycyl-2-Allyl Proline and Treatment of Peripheral Neuropathy". Each of the above applications is expressly incorporated herein fully by reference.

FIELD OF THE INVENTION

The present invention relates to novel bicyclic compounds structurally related to diketopiperazines and methods for their therapeutic use. In particular, this invention relates to the neuroprotective activity of such compounds. More particularly, this invention relates to the use of these compounds and pharmaceutical compositions thereof in the treatment of diseases and conditions characterised by neuronal degeneration and/or death. More particularly, this invention relates to the use of cyclic Glycyl-2-allylProline ("cyclic G-2-allylP" or "cG-2-allylP") and pharmaceutical compositions thereof in the treatment of peripheral neuropathies.

BACKGROUND

Degeneration and/or death of cells in the nervous system are major factors in many diseases and medical conditions. Such diseases and conditions include traumatic brain and spinal cord injuries, stroke, neural perfusion secondary to cardiac arterial bypass graft surgery (CABG), Parkinson's disease, Alzheimer's disease, multiple sclerosis, amyotrophic lateral sclerosis and other neurodegenerative diseases. It is of interest to prevent or decrease such cell death and degeneration.

Certain compounds are useful as neuroprotective agents. One such compound is insulin-like growth factor 1 (IGF-1) (Scheepens et al, WO00/13650). IGF-1 is a naturally occurring peptide that can decrease the binding of glutamate to the glutamate receptors of neurons (Bourguignon, U.S. Pat. No. 5,804,550). IGF-1 can also decrease neuronal degradation caused by damage and disease. IGF-1 is cleaved by proteolysis in vivo to give $des_{1-3}$ IGF-1 and the N-terminal tripeptide Gly-Pro-Glu (GPE). GPE and analogues have been found to be neuroprotective (Gluckman et al, U.S. Pat. No. 6,187,906 incorporated herein by reference).

However, such peptides are far from ideal for the treatment of neural death and degeneration especially as they are rapidly metabolised in vivo. There is a need for compounds that provide neuroprotective and neuroregenerative properties and are more metabolically stable especially as regards resistance to proteases.

A derivative of GPE; cyclic Pro-Gly ("cPG"), a diketopiperazine, has been shown to be neuroprotective and neuroregenerative. cPG was found to prevent toxic neural degeneration and cell death and to promote neurite outgrowth in neurons (Guan et al, PCT/US02/36235 incorporated herein by reference). Diketopiperazine analogues of thyrotropin-releasing hormone (TRH) are known to be neuroprotective (Kozikowski et al WO99/40931).

Peripheral neuropathy is a dysfunction of peripheral nerves the symptoms of which may include varying degrees of sensory disturbances, pain or muscular atrophy, diminished reflexes or vasomotor symptoms (The Merck Manual of Diagnosis and Therapy, 18th ed. 2006). Depending on the distribution of a peripheral neuropathy it can be classified as either a mononeuropathy, most commonly caused by trauma and confined to a single limb or nerve, or a polyneuropathy, a diffuse peripheral nerve disorder. Polyneuropathies can arise from toxic causes (eg, pyridoxine intoxication, chemotherapy), metabolic conditions (eg, AIDS, diabetes mellitus, or cancer) or autoimmune response. Peripheral neuropathy may affect motor, sensory or both types of neural fibres. Sensory peripheral neuropathies are characterized by degeneration of sensory neurons, particularly the large axons of the proximal and distal nerves (large sensory fibre axonopathy). In the cases of lower extremity diabetic neuropathy and vitamin B6-induced peripheral neuropathy, the distal peroneal and sural sensory nerves that descend from the sciatic nerve can be affected. Conduction velocities of the sensory nerves can be decreased, and loss of sensation can lead to functional incapacity, such as gait ataxia (abnormal locomotion).

At present there is a paucity of treatments available for neuropathic conditions, and these are limited to drugs for symptomatic relief of neuropathic pain. The common treatment options include antidepressants, such as duloxetine (which provide some neuropathic pain relief independent of effects on depression) and anticonvulsants, such as gabapentin. These only have appreciable efficacy in a subset of patients, and no disease-modifying or disease-halting drugs are currently available. A disease-modifying treatment for neuropathy in a chronic condition such as diabetes would need to be given throughout the course of the disease to prevent its progression. Given the chronic nature of such treatment, any potential drug should be suitable for oral delivery.

SUMMARY

Embodiments of this invention include novel diketopiperazines that are structurally related to cPG.

One aspect of this invention provides novel cyclic compounds having the structural formulas and substituents described below.

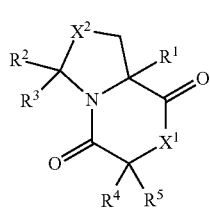

Formula 1

In some aspects, compounds of Formula 1 include substituents where:

$X^1$ is selected from the group consisting of NR', O and S;

$X^2$ is selected from the group consisting of CH$_2$, NR', O and S;

$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —CH$_2$—(CH$_2$)$_n$—CH$_2$— where n is an integer from 0-6; or $R^2$ and $R^3$ taken together are —CH$_2$—(CH$_2$)$_n$—CH$_2$— where n is an integer from 0-6; with the proviso that when $R^1$=methyl and $R^2$=$R^3$=$R^4$=H then $R^5$≠benzyl and; when $R^1$=H, at least one of $R^2$ and $R^3$≠H.

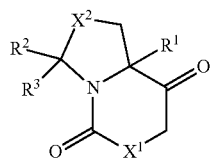

Formula 2

In other aspects, compounds of Formula 2 include substituents where:

$X^1$ is selected from the group consisting of NR', O and S;

$X^2$ is selected from the group consisting of CH$_2$, NR', O and S;

$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, alkenyl, substituted alkenyl, heteroalkyl, substituted heteroalkyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —CH$_2$—(CH$_2$)$_n$—CH$_2$— where n is an integer from 0-6;

with the proviso that at least one R≠H.

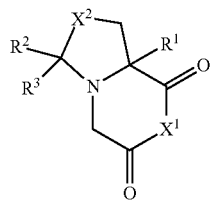

Formula 3

In additional aspects, compounds of Formula 3 include substituents where:

$X^1$ is selected from the group consisting of NR', O and S;

$X^2$ is selected from the group consisting of CH$_2$, NR', O and S;

$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl; or $R^2$ and $R^3$ taken together are —CH$_2$—(CH$_2$)$_n$—CH$_2$— where n is an integer from 0-6.

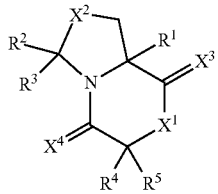

Formula 4

In further aspects, compounds of Formula 4 include substituents where:

$X^1$, $X^3$, and $X^4$ are independently selected from the group consisting of S, O, and NH;

$X^2$ is selected from the group consisting of S, O, CH$_2$ and NH;

$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —CH$_2$—(CH$_2$)$_n$—CH$_2$— where n is an integer from 0-6; or $R^2$ and $R^3$ taken together are —CH$_2$—(CH$_2$)$_n$—CH$_2$— where n is an integer from 0-6; with the proviso that at least one R≠H and that both $X^3$ and $X^4$≠O.

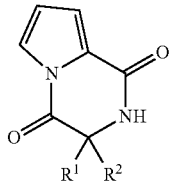

Formula 5

Additionally, other aspects, compounds of Formula 5 include substituents where $R^1$ and $R^2$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^1$ and $R^2$ taken together are —$CH_2$—$(CH_2)_n$—$CH_2$— where n is an integer from 0-6.

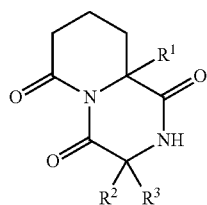

Formula 6

In other aspects, compounds of Formula 6 include substituents where $R^1$, $R^2$ and $R^3$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —$CH_2$—$(CH_2)_n$—$CH_2$— where n is an integer from 0-6.

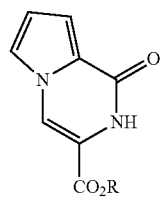

Formula 7

In yet other aspects, compounds of Formula 7 include substituents where R is selected from the group consisting of alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl.

Other aspects of the invention provides pharmaceutically acceptable salts of the compounds described in Formulas 1-7.

In still other aspects, this invention provides pharmaceutical compositions comprising a pharmaceutically acceptable excipient and a therapeutically effective amount of at least one compound of this invention. These compositions find use as anti-apoptotic and anti-necrotic agents and for other conditions involving neural degeneration or injury.

In further aspects, this invention provides methods of treating an animal having a disease or injury capable of treatment by administration of a suitable compound of Formulas 1-7, comprising administration to that animal of at least one compound of this invention to decrease neurodegeneration caused by an injury or disease. In certain other aspects, this invention includes methods for treating an animal with a diketopiperazine of any of Formulas 1-7 in conjunction with at least one other conventional therapeutic agent for the disease being treated.

In yet further aspects, the animal to be treated is a human.

In still further aspects, this invention provides methods of synthesizing, formulating and preparing pharmaceutical preparations comprising compounds of Formulas 1-7 of this invention.

In further aspects, this invention provides a compound of Formula 1 or a pharmaceutically acceptable salt, stereoisomer or hydrate thereof, wherein $R^1$=allyl, $R^2$=$R^3$=$R^4$=$R^5$=H, $X^1$=NH, $X^2$=$CH_2$ (cG-2-allylP).

In still other aspects, this invention provides pharmaceutical compositions comprising a pharmaceutically acceptable excipient and a therapeutically effective amount of cG-2-allylP.

In further aspects, this invention provides methods of treating an animal having a peripheral neuropathy, comprising administration to that animal an effective amount of a composition comprising cG-2-allylP.

In yet further aspects the animal treated is a human being.

The compounds and methods can also be used to treat peripheral neuropathies caused by exposure to toxic substances eg, pyridoxine, alcohol, heavy metals, chemotherapeutic agents; metabolic disorders eg, diabetes mellitus, chronic renal insufficiency; or autoimmune disease.

Thus, in addition to other, central, neuroprotective effects demonstrated in U.S. patent application Ser. Nos. 10/570,395, 11/399,974, PCT/US2004/028308, and PCT/US2007/21744, this invention includes expanded uses of diketopiperazines for treatment of disorders of the peripheral nervous system.

BRIEF DESCRIPTION OF THE DRAWINGS

This invention is described with reference to specific embodiments thereof. Other aspects of this invention can be appreciated with reference to the drawings, in which.

DETAILED DESCRIPTION

Definitions

Figure 1:
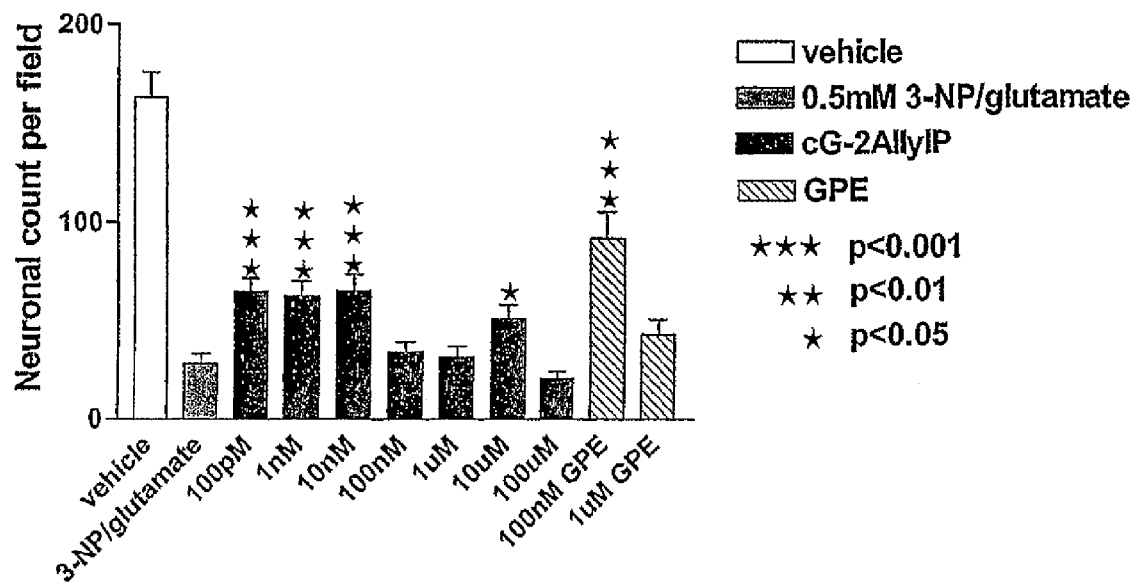
FIG. 1 is a graph showing effects of cyclic G-2allylP on neuronal survival in animals following excitotoxic oxidative stress.

"Alkenyl" refers to an unsaturated branched, straight chain or cyclic hydrocarbon radical having at least one carbon-carbon double bond. The radical may be in either the cis or trans conformation about the double bond(s). Exemplary alkenyl groups include allyl, ethenyl, propenyl, isopropenyl, butenyl, isobutenyl, cyclopentenyl and the like. In some embodiments the alkenyl groups are ($C_2$-$C_6$) alkenyl, and in other embodiments, allyl can be particularly useful.

"Alkyl" refers to a saturated branched, straight chain or cyclic hydrocarbon radical. Exemplary alkyl groups include methyl, ethyl, isopropyl, cyclopropyl, tert-butyl, cyclopropylmethyl, hexyl and the like. In some embodiments the alkyl groups are ($C_1$-$C_6$) alkyl.

"Alkynyl" refers to an unsaturated branched, straight chain or cyclic hydrocarbon radical having at least one carbon-carbon triple bond. Exemplary alkynyl groups include ethynyl, propynyl, butynyl, isobutynyl and the like. In some embodiments the alkynyl group is ($C_2$-$C_6$) alkynyl.

"Aryl" refers to an unsaturated cyclic hydrocarbon radical with a conjugated π electron system. Exemplary aryl groups include phenyl, naphthyl and the like. In some embodiments the aryl group is ($C_5$-$C_{20}$) aryl.

"Arylalkyl" refers to a straight chain alkyl, alkenyl or alkynyl group wherein one of the hydrogen atoms bound to the terminal carbon is replaced with an aryl group. Exemplary arylalkyl groups include benzyl, naphthylmethyl, benzylidene and the like.

"Growth factor" refers to an extracellularly active polypeptide that stimulates a cell to grow or proliferate by interacting with a receptor on the cell.

"Heteroalkyl" refers to an alkyl moiety wherein one or more carbon atoms are replaced with another atom such as N, P, O, S etc. Exemplary heteroalkyl groups include pyrrolidine, morpholine, piperidine, piperazine, imidazolidine, pyrazolidine, tetrahydrofuran, ($C_1$-$C_{10}$) substituted amines, ($C_2$-$C_6$) thioethers and the like.

"Heteroaryl" refers to an aryl moiety wherein one or more carbon atoms are replaced with another atom such as N, P, O, S etc. Exemplary heteroaryl groups include carbazole, furan, imidazole, indazole, indole, isoquinoline, purine, pyrazine, pyrazole, pyridazine, pyridine, pyrrole, thiazole, thiophene, triazole and the like.

"Injury" includes any acute or chronic damage of an animal that results in degeneration or death of cells in the nervous system. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

Peripheral neuropathy refers to a dysfunction of peripheral nerves the symptoms of which may include varying degrees of sensory disturbances, pain or muscular atrophy, diminished reflexes or vasomotor symptoms. Peripheral neuropathy includes any peripheral neuropathies induced by: toxin exposure (e.g. induced by exposure to e.g. pyridoxine, heavy metals, chemotherapeutic agents); myelin dysfunction (e.g., caused by immune response to viruses (e.g., HIV), bacteria (e.g., *Campylobacter*) or vaccines (e.g., influenza vaccine) or autoimmune response); compromised vascular supply to the peripheral nerves (e.g., chronic arteriosclerotic ischemia, vasculitis, hypercoagulable states); metabolic states (e.g., diabetes mellitus, chronic renal insufficiency); trauma (e.g., muscular overextension, pressure, compression, hemorrhage, exposure to cold or radiation, direct tumor invasion). It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "pharmaceutically acceptable salt" refers to a salt that is pharmaceutically acceptable and has the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid mono-salt or a di-acid salt; and similarly where there are more than two acidic groups present, some or all of such groups can be present as salts.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "stereoisomer" is a molecule having a chiral center. The term "cyclic G-2-allylProline" includes all stereoisomers.

"Substituted" refers to where one or more of the hydrogen atoms on an alkyl, heteroalkyl, alkenyl, alkynyl, aryl, heteroaryl or arylalkyl radical are independently replaced with another substituent. Substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR')—NR'R', trihalomethyl and halogen where each R' is independently —H, alkyl, heteroalkyl, alkenyl, alkynyl, aryl, arylalkyl, heteroaryl or heteroarylalkyl.

A "therapeutically effective amount" means the amount that, when administered to an animal for treating a disease, is sufficient to effect treatment for a disease or an injury. A "therapeutically effective amount" means an amount that decreases adverse symptoms or findings, promotes desirable symptoms or findings, and/or treats an underlying disorder, and/or is curative.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

Compounds of the Invention

Certain embodiments of this invention include novel derivatives of cPG having structures as described below for Formulas 1-7.

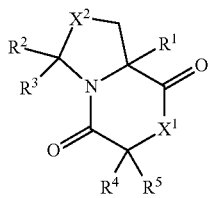

Formula 1

In certain embodiments, compounds of Formula 1 include substituents where:

$X^1$ is selected from the group consisting of NR', O and S;
$X^2$ is selected from the group consisting of $CH_2$, NR', O and S;
$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^4$ and $R^5$ taken together are —$CH_2$—$(CH_2)_n$—$CH_2$— where n is an integer from 0-6;
or $R^2$ and $R^3$ taken together are —$CH_2$—$(CH_2)_n$—$CH_2$— where n is an integer from 0-6; with the proviso that when $R^1$=methyl and $R^2$=$R^3$=$R^4$=H then $R^5$≠benzyl and;
when $R^1$=H, at least one of $R^2$ and $R^3$≠H.

In further embodiments, compounds of Formula 1 include substituents where:
$R^1$=methyl, $R^2$=$R^3$=$R^4$=$R^5$=H, $X^1$=NH, $X^2$=$CH_2$;
$R^1$=allyl, $R^2$=$R^3$=$R^4$=$R^5$=H, $X^1$=NH, $X^2$=$CH_2$;
$R^1$=$R^2$=$R^3$=H, $R^4$=$R^5$=methyl, $X^1$=NH, $X^2$=$CH_2$;
$R^1$=$R^4$=$R^5$=H, $R^2$=$R^3$=methyl, $X^1$=NH, $X^2$=$CH_2$.

In other embodiments of the invention, compounds of Formula 1 include substituents where;
$R^4$ and $R^5$ taken together are —$CH_2$—$(CH_2)_n$—$CH_2$— and:
$R^1$=methyl, $R^2$=$R^3$=H, n=0, $X^1$=NH, $X^2$=$CH_2$;
$R^1$=methyl, $R^2$=$R^3$=H, n=2, $X^1$=NH, $X^2$=$CH_2$;
$R^1$=allyl, $R^2$=$R^3$=H, n=0, $X^1$=NH, $X^2$=$CH_2$;
$R^1$=allyl, $R^2$=$R^3$=H, n=2, $X^1$=NH, $X^2$=$CH_2$.
$R^1$=methyl, $R^2$=$R^3$=H, n=3, $X^1$=NH, $X^2$=$CH_2$;
$R^1$=allyl, $R^2$=$R^3$=H, n=3, $X^1$=NH, $X^2$=$CH_2$.

In still other embodiments of the invention, compounds of Formula 1 include substituents where $R^1$=methyl or allyl, $R^2$=$R^3$=$R^4$=H and $R^5$ is selected from the group consisting of the side chains of the amino acids: alanine, arginine, asparagine, aspartic acid, cysteine, glutamic acid, glutamine, histidine, isoleucine, leucine, lysine, methionine, praline, serine, threonine, tryptophan, tyrosine, valine, norvaline, norleucine, citruline, ornithine, homocysteine, homoserine, alloisoleucine, isovaline, sarcosine and the like.

In yet further embodiments of the invention, compounds of Formula 1 include substituents where:
$R^1$=methyl, $R^2$=$R^3$=methyl, $R^4$=$R^5$=H, $X^1$=NH and $X^2$=S;
$R^1$=allyl, $R^2$=$R^3$=methyl, $R^4$=$R^5$=H, $X^1$=NH and $X^2$=S.

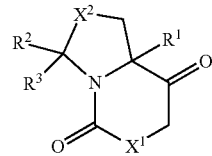

Formula 2

In other embodiments, compounds of Formula 2 include substituents where:

$X^1$ is selected from the group consisting of NR', O and S;
$X^2$ is selected from the group consisting of $CH_2$, NR', O and S;
$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, alkenyl, substituted alkenyl, heteroalkyl, substituted heteroalkyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^2$ and $R^3$ taken together are —$CH_2$—$(CH_2)_n$—$CH_2$— where n is an integer from 0-6; with the proviso that at least one R≠H.

In still other embodiments, compounds of Formula 2 include substituents where:
$R^1$=methyl, $R^2$=$R^3$=H, $X^1$=NH, $X^2$=$CH_2$;
$R^1$=allyl, $R^2$=$R^3$=H, $X^1$=NH, $X^2$=$CH_2$;
$R^1$=ethyl, $R^2$=$R^3$=H, $X^1$=NH, $X^2$=$CH_2$;
$R^1$=H, $R^2$=$R^3$=methyl, $X^1$=NH, $X^2$=$CH_2$.

In another series of embodiments, compounds of Formula 2 include substituents where:
$R^1$=methyl, $R^2$=$R^3$=methyl, $X^1$=NH and $X^2$=S;
$R^1$=allyl, $R^2$=$R^3$=methyl, $X^1$=NH and $X^2$=S.

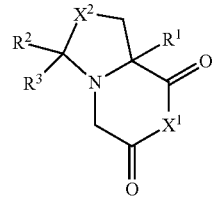

Formula 3

In other embodiments, compounds of Formula 3 include substituents where:

$X^1$ is selected from the group consisting of NR', O and S;

$X^2$ is selected from the group consisting of $CH_2$, NR', O and S;

$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —CH$_2$—(CH$_2$)$_n$—CH$_2$— where n is an integer from 0-6.

In still other embodiments, compounds of Formula 3 include substituents where:

$R^1$=methyl, $R^2$=$R^3$=H, $X^1$=NH, $X^2$=CH$_2$;
$R^1$=allyl, $R^2$=$R^3$=H, $X^1$=NH, $X^2$=CH$_2$;
$R^1$=ethyl, $R^2$=$R^3$=H, $X^1$=NH, $X^2$=CH$_2$;
$R^1$=H, $R^2$=$R^3$=methyl, $X^2$=CH$_2$.

In further embodiments, compounds of Formula 3 include substituents where:

$R^1$=methyl, $R^2$=$R^3$=methyl, $X^1$=NH and $X^2$=S;
$R^1$=allyl, $R^2$=$R^3$=methyl, $X^1$=NH and $X^2$=S.

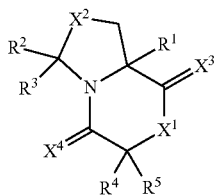

Formula 4

In further embodiments, compounds of Formula 4 include substituents where:

$X^1$, $X^3$, and $X^4$ are independently selected from the group consisting of S, O, and NH;

$X^2$ is selected from the group consisting of S, O, CH$_2$ and NH;

$R^1$, $R^2$, $R^3$, $R^4$ and $R^5$ are independently selected from the group consisting of —H, OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —CH$_2$—(CH$_2$)$_n$—CH$_2$— where n is an integer from 0-6;

or $R^2$ and $R^3$ taken together are —CH$_2$—(CH$_2$)$_n$—CH$_2$— where n is an integer from 0-6;

with the proviso that at least one R≠H and that both $X^3$ and $X^4$≠O.

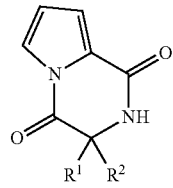

Formula 5

In still further embodiments, compounds of Formula 5 include substituents where $R^1$ and $R^2$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^1$ and $R^2$ taken together are —CH$_2$—(CH$_2$)$_n$—CH$_2$— where n is an integer from 0-6.

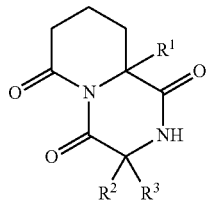

Formula 6

In other aspects, compounds of Formula 6 include substituents where $R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —CH$_2$—(CH$_2$)$_n$—CH$_2$— where n is an integer from 0-6.

In yet other embodiments, compounds of Formula 6 include substituents where $R^1$ is methyl or allyl.

Formula 7

In yet further embodiments, compounds of Formula 7 include substituents where R is selected from the group consisting of alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl.

Those with skill in the art will appreciate that the above structural representations can contain chiral centres, the number of which will depend on the different substituents. The chirality may be either R or S at each centre. The structural drawings can represent only one of the possible tautomeric, conformational isomeric or enantiomeric forms, and it should be understood that the invention encompasses any tautomeric, conformational isomeric or enantiomeric form which exhibit biological or pharmacological activity as described herein.

Pharmacology and Utility

Cyclic Glycyl-2-allylProline (cG-2-allylP) is described in: U.S. Utility application Ser. No. 10/570,395, filed Mar. 2, 2006, entitled "Neuroprotective Bicyclic Compounds and Methods for Their Use"; U.S. Pat. No. 7,776,876 issued Aug. 17, 2010, entitled "Cyclic G-2allylProline in Treatment of Parkinson's Disease"; PCT International Patent Application No: PCT/US2004/028308, entitled "Neuroprotective Bicyclic Compounds and Methods for Their Use"; U.S. provisional Patent Application No. 60/499,956 filed Sep. 3, 2003, entitled "Neuroprotective Bicyclic Compounds and Methods for Their Use"; U.S. Provisional Patent Application Ser. No. 60/851,106, filed Oct. 11, 2006 entitled "Cyclic Clycyl-2AllylProline Improves Cognitive Performance in Impaired Animals"; U.S. Provisional Patent Application Ser. No. 60/852,507, filed Oct. 18, 2006 entitled "Cyclic Glycyl-2Allyl Proline Improves Cognitive Performance in Impaired Rats"; PCT International Patent Application No: PCT/US2007/21744 filed 11 Oct. 2007, entitled "Cyclic Glycyl-2-allylProline Improves Cognitive Performance in Impaired Animals"; and U.S. Utility application Ser. No. 12/421,871 filed Apr. 10, 2009 entitled "Cyclic Glycyl-2-allylProline Improves Cognitive Performance in Impaired Animals". Each of the above patent applications is expressly incorporated herein fully by reference.

Certain aspects of this invention include the use of compounds of the invention in treatment or prevention of cell damage, degeneration and/or death in mammals in response to injury or disease. Some embodiments comprise delivering a composition containing a compound of the invention to an animal suffering from neural degeneration, and in some cases, conditions involving apoptotic and necrotic cell death. In some embodiments, compositions are desirable to treat an injury or disease of the CNS affecting or liable to affect brain cells. Compositions are provided that can also include one or more other agents that promote neural regeneration, decrease cell degeneration or death, or are neuroprotective.

Such other agents may be selected from the group consisting of for example, growth factors and associated derivatives, e.g., insulin-like growth factor-I [IGF-I], insulin-like growth factor-II [IGF-II], the tripeptide GPE, transforming growth factor-β1, activin, growth hormone, nerve growth factor, growth hormone binding protein, and/or IGF-binding proteins.

Other aspects of the invention include compositions and methods of promoting fasiculation of axons. By promoting formation of nerve bundles, compounds of the invention may be useful in treating conditions in which nerve processes (axons and/or dendrites) have become severed, such as in sharp force injuries, local areas of necrosis or disease, or other localized injuries to nerve processes.

In yet other embodiments, compositions and methods to treat or prevent cell damage and death in response to injury and disease, including CNS injury and disease, comprise administration of a therapeutic amount of a compound of the invention alone or in combination with other agents, after the insult. These embodiments can be particularly desirable in situations of unexpected injury, such as in cardiac arrest, trauma such as head injuries caused by automobile accidents, head wounds and the like.

In still further embodiments, compounds of the invention can be used either alone or in combination with other agents to prevent adverse effects of planned brain injury. Such conditions include CABG or other planned surgeries such as brain surgery, vascular surgery or other interventions that may lead to decreased perfusion of the nervous system. By treating an animal, such as a human being, in advance and/or simultaneously and/or after the surgery, adverse neurological effects can be ameliorated.

As indicated above, the present invention is broadly based upon the applicant's finding that compounds of the invention can protect cells, particularly nerve cells, against damage, loss of neurites, and/or apoptotic or necrotic cell death.

It is herein demonstrated that compounds of the invention exhibit neuroprotection in both cell culture and in animal models of neurodegenerative disease and can therefore be an effective addition or alternative to conventional therapies for neural degeneration.

Although the mechanism of the protective effects is not known, one possible mechanism involves protecting cells from apoptotic and necrotic cell death. However, regardless of the mechanism of action, compounds of the invention can be used as an effective therapy for a variety of neurological diseases, including hypoxia, ischemia and neurotoxin-induced nerve damage. Moreover, compounds of the invention can be used in the absence of any particular neurological deficit to promote neurite outgrowth and fasiculation of nerves. Thus, in situations in which cell death is not necessarily associated with the neurological disorder (e.g., axonal damage such as caused by spinal cord injury), administration of compounds of the invention may be an effective way of promoting neurite regeneration.

Therapeutic Applications

Compositions and methods of the invention find use in the treatment of animals, such as human patients, suffering from neural injury or disease. Still more generally, the compositions and methods of the invention find use in the treatment of mammals, such as human patients, suffering from nerve damage or potential apoptotic and/or necrotic cell death, due to injuries and diseases.

Specific conditions and diseases characterised by neuronal degeneration, apoptosis and/or necrosis include but are not limited to Alzheimer's disease, Parkinson's disease, multiple sclerosis, amyotrophic lateral sclerosis, spinal muscular atrophy, toxin-induced peripheral neuropathy, pyridoxine-induced peripheral neuropathy, diabetic peripheral neuropathy, Creutzfeldt-Jakob disease, AIDS dementia, progressive supranuclear palsy, myelinopathia centralis diffusa (vanishing white matter disease), chronic neurodegenerative disease, Huntington's disease, stroke, ischemic injury, hypoxic injury, reperfusion injury, head injury, CNS trauma, epilepsy, cerebral ischemia, glaucoma, retinal disorders, optic neuropathy, optic neuritis, Down's syndrome, encephalomyelitis, meningitis, panencephalitis, neuroblastoma, schizophrenia and depression. Each of the above conditions exhibits pathophysiological findings and symptoms that are mimicked by neurotoxicity associated with glutamate toxicity.

Still more generally, the invention has application in the induction of nerve bundle formation following insult in the form of trauma, toxin exposure, asphyxia or hypoxia-ischemia. Additionally, the invention has application in the treatment or prevention of apoptosis in response to injury or disease in the form of cancers, viral infections, autoimmune diseases, neurological diseases and injuries and cardiovascular diseases.

Treatment may be given before an injury, for example, before elective surgery. Examples of relevant elective procedures include neural surgery, in which retraction of lobes of the brain may lead to cerebral oedema, or heart operations, such as valve replacement, in which inevitable small emboli are said to lead to detectable impairment of brain function in some 75% of cases.

Compositions and methods of the invention find use in the treatment of animals, such as human patients, suffering from peripheral neuropathy. Still more generally, the compositions and methods of the invention find use in the treatment of mammals, such as human patients, suffering from peripheral neuropathy caused by diabetes (diabetic peripheral neuropathy), and toxicities caused by, for example, heavy metals, chemotherapeutic agents or vitamin excess (e.g., pyridoxine). These conditions have numerous features in common, as shown in Table 1 below.

TABLE 1

Comparison of Features of Peripheral Neuropathies

|  | Pyridoxine (Vitamin B6) Intoxication | Streptozotocin-Induced Diabetic Neuropathy | Diabetic Peripheral Neuropathy | Chemotherapy-Induced Peripheral Neuropathy |
|---|---|---|---|---|
| Model Condition | Experimental Model & Clinical Condition | Experimental Model | Clinical Condition | Experimental Model & Clinical Condition |
| Principle Pathology | Reversible peripheral nerve axonopathy, resulting in reduced sensory fiber conduction velocity, restricted to large diameter cells, without demyelination. [1, 2, 3, 4, 5, 6] | Peripheral nerve axonopathy, resulting in reduced autonomic and sensory fiber conduction velocity, with degeneration being fiber length dependent. [11, 12, 13] | Progressive peripheral nerve axonopathy, resulting in reduced sensory fiber conduction velocity, with degeneration being fiber length dependent. [19, 20, 21] | Peripheral nerve neuronopathy, as well as damage to dorsal root ganglia, resulting in reduced sensory fiber conduction velocity, with and without demyelination. [22, 23] |
| Proposed Mechanism of Toxicity | Saturation of pyridoxal kinase in the liver may inhibit neuronal pyridoxal phosphate, altering neuronal metabolism. Impaired neuronal metabolism leads to an impoverished energy support of the large axons. [2, 3] | Selective toxicity to islet β-cells of the pancreas leading to a hyperglycemic diabetic condition, with resulting neurotoxicity, as in clinical diabetes. [14, 15, 16] | Wallerian axonal degeneration resulting from hyperglycemic neurotoxicity. Raised glucose favors metabolism through the polyol pathway that results in production of oxidative stress. [16, 19, 20] | (For platinum compounds) Disturbance of metabolism and axonal transport in peripheral sensory nerves following accumulation in the DRG leads to axonopathy. [22, 24] |
| Peripheral Nerves Affected | Primarily large descending sensory nerves, including peroneal and sural nerves that descend from the sciatic. [3, 6, 7] | Primarily autonomic and sensory nerves, including peroneal and other nerves descending from the sciatic. [11, 13] | Primarily large descending sensory nerves, including peroneal and sural nerves that descend from the sciatic. [19, 20] | Primarily large descending sensory nerves, including peroneal and sural nerves that descend from the sciatic. [22, 23] |

Table 1 References
The numbers in brackets in Table 1 above refer to the references below.
[1] Schaumburg H, Kaplan J, Windebank A, Vick N, Rasmus S, Pleasure D, Brown M J (1983) Sensory neuropathy from pyridoxine abuse. A new megavitamin syndrome. N. Engl. J. Med. 309: 445-448.
[2] Krinke G, Naylor D C, Skorpil V (1985) Pyridoxine megavitaminosis: an analysis of the early changes induced with massive doses of vitamin B6 in rat primary sensory neurons. J Neuropathol. Exp. Neurol. 44: 117-129.
[3] Windebank A J, Low P A, Blexrud M D, Schmelzer J D, Schaumburg H H (1985) Pyridoxine neuropathy in rats: specific degeneration of sensory axons. Neurology 35: 1617-1622.
[4] Albin R L, Albers J W, Greenberg H S, Townsend J B, Lynn R B, Burke Jr. J M, Alessi A G (1987) Acute sensory neuropathy-neuronopathy from pyridoxine overdose. Neurology 37: 1729-1732.
[5] Dalton K, Dalton M J (1987) Characteristics of pyridoxine overdose neuropathy syndrome. Acta Neurol. Scand. 76: 8-11.
[6] Xu Y, Sladky J T, Brown M J (1989) Dose-dependent expression of neuropathy after experimental pyridoxine intoxication. Neurology 39: 1077-1083.
[7] Perry T A, Weerasuriya A, Mouton P R, Holloway H W, Greig N H (2004) Pyridoxine-induced toxicity in rats: a stereological quantification of the sensory neuropathy. Exp Neurol. 190: 133-144.
[8] Helgren M E, Cliffer K D, Torrento K, Cavnor C, Curtis R, Distefano P S, Wiegand S J, Lindsay R M (1997) Neurotrophin-3 administration attenuates deficits of pyridoxine-induced large-fiber sensory neuropathy. J. Neurosci. 17: 372-382.
[9] Callizot N, Warter J-M, Poindron P (2001) Pyridoxine-induced neuropathy in rats: a sensory neuropathy that responds to 4-methylcatechol. Neurobiol. Dis. 8: 626-635.
[10] Perry T A, Holloway H W, Weerasuriya A, Mouton P R, Duffy K, Martinson J A, Greig N H (2007) Evidence of GLP-1-mediated neuroprotection in an animal model of pyridoxine-induced peripheral sensory neuropathy. Exp. Neurology 203: 293-303.
[11] Jakobsen J, Lundbæk K. (1976) Neuropathy in experimental diabetes: an animal model. Br. Med. J. 2: 278-279
[12] Bell R H, Hye R J (1983) Animal models of diabetes mellitus: physiology and pathology. J. Surg. Res. 35: 433-460.
[13] Mattingly G E, Fischer V W. (1983) Peripheral neuropathy following prolonged exposure to streptozotocin-induced diabetes in rats: a teased nerve fiber study. Acta Neuropathol. 59: 133-138.
[14] Szkudelski T (2001) The mechanism of alloxan and streptozotocin action in B cells of the rat pancreas. Physiol. Res. 50: 536-546.
[15] Schmeichel A M, Schmelzer J D, Low P A (2003) Oxidative injury and apoptosis of dorsal root ganglion neurons in chronic experimental diabetic neuropathy. Diabetes 52: 165-171.

TABLE 1-continued

Comparison of Features of Peripheral Neuropathies

| | Pyridoxine (Vitamin B6) Intoxication | Streptozotocin-Induced Diabetic Neuropathy | Diabetic Peripheral Neuropathy | Chemotherapy-Induced Peripheral Neuropathy |
|---|---|---|---|---|

[16] Tomlinson D R, Gardiner N J (2008) Glucose neurotoxicity. Nature Neurosci. Rev. 9: 36-45.
[17] Wuarin-Bierman L, Zahnd G R, Kaufmann F, Burcklen L, Adler J. (1987) Hyperalgesia in spontaneous and experimental animal models of diabetic neuropathy. Diabetologia. 30: 653-658.
[18] Courteix C, Eschalier A, Lavarenne J. (1993) Streptozocin-induced diabetic rats: behavioural evidence for a model of chronic pain. Pain. 53: 81-88.
[19] Dyck P J, Giannini C. (1996) Pathologic alterations in the diabetic neuropathies of humans: a review. J. Neuropathol. Exp. Neurol. 55: 1181-1193.
[20] Yagihashi S, Yamagishi S-I, Wada R. (2007) Pathology and pathogenic mechanisms of diabetic neuropathy: correlation with clinical signs and symptoms. Diab. Res. Clin. Prac. 77S: S184-S189.
[21] Chong M S, Hester J (2007) Diabetic painful neuropathy. Current and future treatment options. Drugs 67: 569-585.
[22] Quasthoff S, Hartung H P (2002) Chemotherapy-induced peripheral neuropathy. J. Neurol 249: 9-17.
[23] Windebank A J, Grisold W. (2008) Chemotherapy-induced neuropathy. J. Peripher. Nerv. Syst. 13: 27-46.
[24] Gregg R W, Molepo J M, Monpetit V J, Mikael N Z, Redmond D, Gadia M, Stewert D J. (1992) Cisplatin neurotoxicity: the relationship between dosage, time, and platinum concentration in neurologic tissues, and morphologic evidence of toxicity. J. Clin. Oncol. 10: 795-803.

Determining Efficacy

The anti-apoptotic and anti-necrotic activity of compounds of the invention on cellular death can be measured in vivo using cell counts by methods known to those skilled in the art including the methods of Klempt et al (Klempt et al; 1992, *Molecular Brain Research:* 13: 93-101), microscopic examinations of morphology, cell counts of surviving and dead neurons stained with thionin/fuchsin and the like. Compounds of the invention can also be measured in vitro using mass spectroscopy, immunological, or chromatographic methods known in the art.

CNS damage may for example be measured clinically by the degree of permanent neurological deficit, cognitive function, and/or propensity to seizure disorders. Herein are disclosed histological techniques suitable for measuring effects in vivo.

The therapeutic ratio of a compound is understood to be the ratio of (1) the mean dose that causes adverse side effect over (2) the mean dose that causes a desirable therapeutic effect. Thus, for compounds that have therapeutic effects at relatively low doses and undesirable side effects at high doses, the therapeutic ratio is >1. Therapeutic ratio can be determined, for example, by comparing the dose that produces significant weight loss (or other observable side-effect) divided by the dose that produces anti-apoptotic and anti-necrotic activity in a suitable in vivo animal species such as the rat or mouse. Suitable animal systems useful for determining therapeutic effects of compounds of this invention include hypoxic-ischemic injury (Sirimanne et al, 1994 *Journal of Neuroscience Methods:* 55: 7-14), experimental immune encephalomyelitis (Mendel et al., 1995 *Eur. J. Immunol.:* 25: 1951-1959) and glutamate toxicity.

Pharmaceutical Compositions and Administration

Compounds of the invention can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount may vary widely depending on the disease or injury, its severity, the age and relative health of the animal being treated, the potency of the compound(s), and other factors. As anti-apoptotic and anti-necrotic agents, therapeutically effective amounts of compounds of this invention may range from 0.01 to 100 milligrams per kilogram mass of the animal, with lower doses such as 0.01 to 10 mg/kg being appropriate for administration through the cerebrospinal fluid, such as by intracerebroventricular administration, and higher doses such as 0.1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Compounds of the invention may be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g. amounts which eliminate or reduce the patient's pathological condition) to provide therapy for the neurological diseases described above.

Desirably, if possible, when administered as anti-apoptotic and anti-necrotic agents, compounds of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.1 percent by weight (% w/w) to 50% w/w of the compound of this invention, preferably 1% w to 25% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animals' CNS, a compound may be injected directly into a site of neural damage. Such routes of administration may be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intraveneously, direct injection into the desired location or other routes.

The effective amount of compound in the CNS may be increased by administration of a pro-drug form of a compound which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In further embodiments of the invention, restoring nerve function in an animal can comprise administering a therapeutic amount of a compound of the invention in combination with another neuroprotective agent, selected from, for example, Glycyl-Prolyl-Glutamate (GPE), Glycyl-2-Methyl Prolyl Glutamate, Glycyl L-thia-5,5-dimethylprolyl-L-glutamic acid (G-thiadiMePE), growth factors and associated derivatives (insulin-like growth factor-I [IGF-I], insulin-like growth factor-II [IGF-II], transforming growth factor-β1, activin, growth hormone, nerve growth factor, growth hormone binding protein, IGF-binding proteins [especially IGFBP-3], basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived neurotrophic factor (BDNF), neurotrophin 3, neurotrophin 4, bone morphogenetic protein 2 [BMP-2], glial-cell line derived neurotrophic factor, activity-dependant neurotrophic factor, cytokine leukaemia inhibiting factor, oncostatin M, interleukin), α-, β-, γ-, or consensus interferon, and TNF-α. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue [ORG 2766] and dizolcipine [MK-801], selegiline; glutamate antagonists such as, NPS1506, GV1505260, MK-801, GV150526; AMPA antagonists such as 2,3-dihydroxy-6-nitro-7-sulfamoylbenzo (f)quinoxaline (NBQX), LY303070 and LY300164; anti-inflammatory agents directed against the addressin MAdCAM-1 and/or its integrin α4 receptors (α4β1 and α4β7), such as anti-MAdCAM-1 mAb MECA-367 (ATCC accession no. HB-9478).

A compound is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773, 919; EP 58,481), copolymers of L-glutamic acid and gamma-ethyl-L-glutamate (Sidman et al., 1983, *Biopolymers:* 22: 547-56), poly(2-hydroxyethyl methacrylate) (Langer et al., 1981, *J. Biomed. Mater. Res.:* 15: 267), ethylene vinyl acetate (Langer et al., 1981, *J. Biomed. Mater. Res.:* 15: 267), or poly-D-(−)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544, 545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment the compound is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. Generally, the formulations are prepared by contacting the compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

A compound is typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Formulations of the compound in pharmaceutical compositions can also include adjuvants. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

For injection, intraventricular administration, and other invasive routes of administration, the compounds used must be sterile. Sterility may be accomplished by any method known in the art, for example filtration through sterile filtration membranes (e.g., 0.2 micron membranes), Therapeutic compositions generally are placed into a container having a sterile access port, for example, an intravenous solution bag or vial having a stopper able to be pierced by a hypodermic injection needle.

A pharmaceutical formulation ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

Preparation of the Compounds

Starting materials and reagents used in preparing these compounds are either available from commercial suppliers such as Aldrich Chemical Company (Milwaukee, Wis.), Sachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, 4$^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and compounds of this invention may be isolated and purified using conventional techniques, including filtration, distillation, crystallization, chromatography, and the like. They may be characterized using conventional methods, including physical constants and spectral data.

Compounds of this invention may be prepared by the methods described below and as given in the Examples.

Compounds of this invention are generally cyclic dipeptides (bicyclic 2,5-diketopiperazines) or analogues thereof. In general, they may be prepared by methods such as are already well-known to persons of ordinary skill in the art of peptide and modified peptide synthesis, following the reaction schemes set forth in the Figures following this specification, or by following other methods well-known to those of ordinary skill in the art of the synthesis of peptides and analogues. See for example, Bodansky: Principles of Peptide Synthesis, Berlin, N.Y.: Springer-Verlag 1993.

Synthesis of the diketopiperazine compounds of this invention may be by solution-phase synthesis as discussed in the Examples or via the solid-phase synthesis method exemplified by Merrifield et al. 1963 *J. Amer. Chem. Soc.*: 85, 2149-2156. Solid phase synthesis may be performed using commercial peptide synthesizers, such as the Applied Biosystems Model 430A, using the protocols established for the instrument.

Specific examples of diketopiperazine synthesis can be found in the Examples following and in, for example, Fischer, 2003, *J. Peptide Science:* 9: 9-35 and references therein. A person of ordinary skill in the art will have no difficulty, taking account of that skill and the knowledge available, and of this disclosure, in developing one or more suitable synthetic methods for compounds of this invention.

The choice of appropriate protecting groups for the method chosen (solid-phase or solution-phase), and of appropriate substrates if solid-phase synthesis is used, will be within the skill of a person of ordinary skill in the art. Appropriate protecting groups for peptide synthesis include t-butyloxycarbonyl (Boc), fluorenylmethyloxycarbonyl (Fmoc), Benzyl (Bzl), t-amyloxycarbonyl (Aoc), tosyl (Tos), benzyloxycarbonyl (Z or Cbz), o-bromo-benzyloxycarbonyl (BrZ) and the like. Additional protecting groups are identified in Merrifield, cited above, as well as in McOmie JFW: Protective Groups in Organic Chemistry, Plenum Press, New York, 1973.

The choice of coupling agent for the method chosen will also be within the skill of a person of ordinary skill in the art. Suitable coupling agents include DCC(N,N'-Dicyclohexylcarbodiimide), Bop (Benzotriazole-1-yl-oxy-tris-(dimethylamino)-phosphonium hexafluorophosphate), PyBop (Benzotriazol-1-yl-oxytripyrrolidinophosphonium hexafluorophosphate), BopCl (bis(2-oxo-3-oxazolidinyl) phosphinic chloride), 2-Chloro-1,3-dimethylimidazolidinium hexafluorophosphate (CIP) and the like.

For example, compounds may be synthesized by the following methods.

Scheme 1: Reagents, conditions and yields:

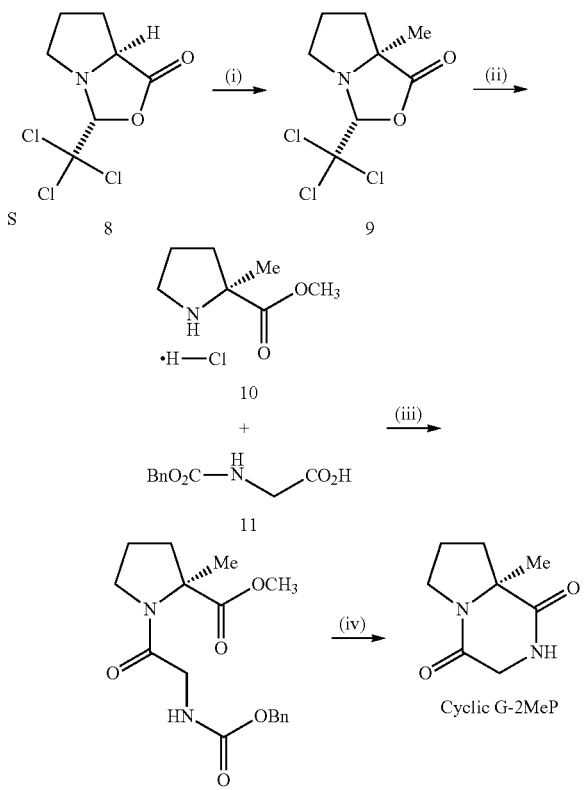

(i) LDA, THF, -78° C., iodomethane, -78 -> -50° C., 2 h (63%);
(ii) SOCl$_2$, CH$_3$OH, reflux, N$_2$, 2.5 h (98%);
(iii) Et$_3$N, BoPCl, CH$_2$Cl$_2$, RT, N$_2$, 20.5 h (78%);
(iv) 10% Pd/C, CH$_3$OH, RT, 15 h (98%).

Oxazolidinone 8 can be synthesized by reaction of chloral with proline. This oxazolidinone can then be reduced using lithium diisopropylamide (LDA), followed by addition of a methyl group using iodomethane to produce oxazolidinone 9. Thionyl chloride or acetyl chloride can be used to produce the methyl ester of 2-methyl proline as in Scheme 1 above. It will be apparent to those skilled in the art that the iodomethane can be replaced with a suitable halogen compound to produce various analogues modified at the carbon 2 position. For example, use of iodoethane will produce 2-ethyl proline; use of allylbromide will produce 2-allyl proline and use of benzylbromide will produce 2-benzyl proline.

The praline protected at the C-terminus can then be coupled to an amino acid protected at the N-terminal with a suitable protecting group such as Cbz, Boc or Fmoc. Suitable coupling reagents for this procedure will be apparent to those skilled in the art and include such reagents as bis(2-oxo-3-oxazolidinyl)phosphinic chloride (BoPCl), dicyclohexylcarbodiimide (DCC), 2-Chloro-1,3-dimethylimidazolidinium hexafluorophosphate (CIP) (Babu and Ananda, 2001, *Indian J. Chem. Sect. B.,*: 40B(1): 70; Akaji and Aimoto 2001, *Tetrahedron*, 57(9), 1749). The dipeptide thus formed can then be selectively de-protected at the N-terminus, using for example, hydrogenation to remove Cbz groups and trifluoroacetic acid (TFA) to remove Boc groups. The molecule then cyclises with elimination of the methoxy group of the methyl ester to give the diketopiperazine.

The amino acid used in scheme 1 is glycine which gives compounds of formula 1 where $R^4=R^5=H$. Replacement of glycine with other amino acids will result in compounds of formula 1 where $R^4=H$ and $R^5$ is equivalent to the side chain of the respective amino acid.

1-Aminocyclohexanecarboxylic acid 13 (Fluka) can be protected at the N-terminus using a protecting group such as Cbz. This compound can then be coupled to a proline derivative suitably protected at the C-terminus using a suitable coupling agent such as 2-Chloro-1,3-dimethylimidazolidinium hexafluorophosphate (CIP) as in Scheme 2. The dipeptide thus formed can then be selectively de-protected at the N-terminus via hydrogenation for example, and the resultant elimination of the methoxy group of the methyl ester produces the diketopiperazine. It will be apparent to those skilled in the art that replacement of the 1-aminocyclohexanecarboxylic acid with analogous compounds such as 1-aminocyclopentanecarboxylic acid or 1-aminocyclopropanecarboxylic acid will be possible. It will also be apparent that the methyl group at the C-2 (carbon centre 8a in scheme 2) position of proline may be replaced with other substituents such as ethyl, allyl and benzyl as discussed above.

All patent and literature references cited throughout the specification are expressly incorporated by reference in their entirety.

EXAMPLES

The present invention is further illustrated by the following examples: These examples are offered by way of illustration only and are not intended to limit the scope of the invention. They are intended only to provide guidance to persons of skill in the art. Other specific embodiments may be carried out within the scope of this invention.

General Methods

Flash chromatography was performed using Scharlau 60 (40-60 μm mesh) silica gel. Analytical thin layer chromatography was carried out on 0.20 mm pre-coated silica gel plates (ALUGRAM® SIL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$ g$^{-1}$. Samples were prepared in the solvent indicated at the concentration specified (measured in g/100 cm$^3$). IR spectra were recorded on a Perkin Elmer Spectrum One FT-IR spectrometer. The samples were prepared as thin films on sodium chloride discs or as solids in potassium bromide discs. A broad signal indicated by br. The frequencies (υ) as absorption maxima are given in wavenumbers (cm$^{-1}$).

NMR spectra were recorded on a Bruker AVANCE DRX400 ($^1$H, 400 MHz; $^{13}$C, 100 MHz) or a Bruker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position ($δ_H$), relative integral, multiplicity (s=singlet, d=doublet, t=triplet, dd=doublet of doublets, m=multiplet, br=broad), coupling constant (J/Hz) and assignment. For $^{13}$C NMR data, chemical shifts are described in parts per million relative to CDCl$_3$ and are reported consecutively as position ($δ_C$), degree of hybridization as determined by DEPT experiments, and assignment. $^1$H NMR spectra were referenced internally using SiMe$_4$ (δ 0.00) or CDCl$_3$ (δ 7.26). $^{13}$C NMR spectra were referenced internally using CDCl$_3$ (δ 77.0). When two sets of peaks arise in the NMR spectra due to different conformations around the glycine-proline amide bond, the chemical shift for the minor cis conformer is marked with an asterisk (*).

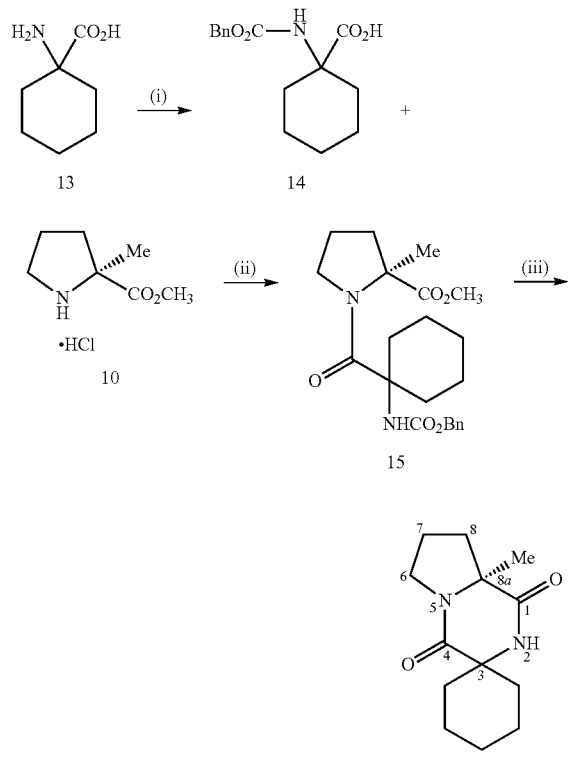

Scheme 2: Reagents, conditions and yields:

Cyclic cyclohexyl-G-2MeP (i) BnO$_2$CCl, Na$_2$CO$_3$, H$_2$O-dioxane (3:1), 19 h, 96%;
(ii) Et$_3$N, HOAt, CIP, 1,2-dichloroethane, reflux, N$_2$, 19 h (23%);
(iii) 10% Pd/C, CH$_3$OH, RT, 17 h (65%).

Accurate mass measurements were recorded on a VG-70SE mass spectrometer.

Hexane and dichloromethane were distilled prior to use. Methanol was dried using magnesium turnings and iodine, and distilled under nitrogen. Triethylamine was dried over calcium hydride and distilled under nitrogen.

Example 1

Synthesis of (8aS)-Methyl-hexahydropyrrolo[1,2-a]pyrazine-1,4-dione (Cyclic G-2MeP)

Scheme 1: Reagents, conditions and yields:

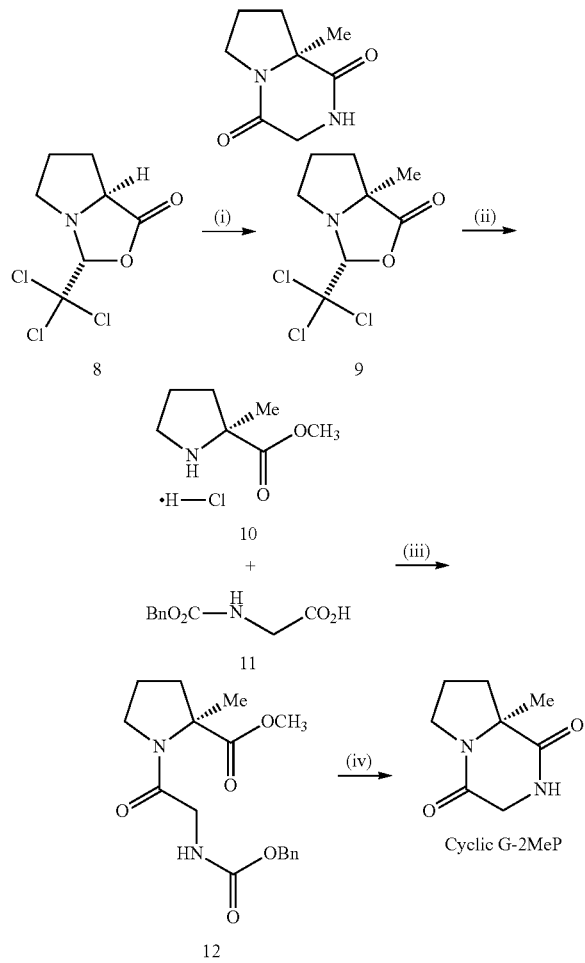

(i) LDA, THF, -78° C., iodomethane, -78 -> -50° C., 2 h (63%);
(ii) SOCl$_2$, CH$_3$OH, reflux, N$_2$, 2.5 h (98%);
(iii) Et$_3$N, BoPCl, CH$_2$Cl$_2$, RT, N$_2$, 20.5 h (78%);
(iv) 10% Pd/C, CH$_3$OH, RT, 15 h (98%).

(2R,5S)-4-Methyl-2-trichloromethyl-1-aza-3-oxabicyclo[3.3.0]octan-4-one 9 n-BuLi (1.31 M, 4.68 cm$^3$, 6.14 mmol) was added dropwise to a stirred solution of diisopropylamine (0.86 cm$^3$, 6.14 mmol) in dry tetrahydrofuran (10 cm$^3$) at −78° C. under an atmosphere of nitrogen. The solution was stirred for 5 min, warmed to 0° C. and stirred for 15 min. The solution was then added dropwise to a solution of oxazolidinone 8 (1.00 g, 4.09 mmol) in dry tetrahydrofuran (20 cm$^3$) at −78° C. over 20 min (turned to a dark brown colour), stirred for a further 30 min then iodomethane (0.76 cm$^3$, 12.3 mmol) was added dropwise over 5 min. The solution was warmed to −50° C. over 2 h. Water (15 cm$^3$) was added and the solution warmed to room temperature and extracted with chloroform (3×40 cm$^3$). The combined organic extracts were dried (MgSO$_4$), filtered and evaporated to dryness in vacuo to give a dark brown semi-solid. Purification of the residue by flash column chromatography (15% ethyl acetate-hexane) afforded oxazolidinone 9 (0.67 g, 63%) as a pale yellow solid: mp 55-57° C. (lit., 57-60° C.); δ$_H$ (300 MHz, CDCl$_3$) 1.53 (3H, s, CH$_3$), 1.72-2.02 (3H, m, Proβ-H and Proγ-H$_2$), 2.18-2.26 (1H, m, Proβ-H), 3.15-3.22 (1H, m, Proδ-H), 3.35-3.44 (1H, m, Proδ-H) and 4.99 (1H, s, NCH).

Methyl L-2-methylprolinate hydrochloride 10 a) Using Acetyl Chloride

Oxazolidinone 9 (0.60 g, 2.33 mmol) was dissolved in dry methanol (15 cm$^3$) under an atmosphere of nitrogen and acetyl chloride (0.33 cm$^3$, 4.66 mmol) was added dropwise to the ice-cooled solution. The solution was heated under reflux for 4.5 h, then the solvent removed under reduced pressure to give a brown oil which was purified by flash column chromatography (10% CH$_3$OH—CH$_2$Cl$_2$) affording the hydrochloride 10 (0.2 g, 48%) as a flaky white solid: mp 107-109° C. (lit., 106-108° C.); δ$_H$ (300 MHz, CDCl$_3$) 1.81 (3H, s, CH$_3$), 1.93-2.14 (3H, m, Proβ-H$_A$H$_B$ and Proγ-H$_2$), 2.33-2.39 (1H, m, Proβ-H$_A$H$_B$), 3.52-3.56 (2H, m, Proδ-H$_2$) and 3.82 (3H, s, CO$_2$CH$_3$).

b) Using Thionyl Chloride

An ice-cooled solution of oxazolidinone 9 (53 mg, 0.21 mmol) in dry methanol (1 cm$^3$) was treated dropwise with thionyl chloride (0.045 cm$^3$, 0.62 mmol). The solution was heated under reflux for 2.5 h, cooled and the solvent removed under reduced pressure to yield a brown oil. The oil was dissolved in toluene (5 cm$^3$), concentrated to dryness to remove residual thionyl chloride and methanol then purified by flash column chromatography (10% CH$_3$OH—CH$_2$Cl$_2$) to afford the hydrochloride 10 (16 mg, 43%) as a flaky white solid. The $^1$H NMR assignments were in agreement with those reported above.

Methyl-N-benzyloxycarbonyl-glycyl-L-2-methylprolinate 12

Dry triethylamine (0.27 cm$^3$, 1.96 mmol) was added dropwise to a solution of hydrochloride 10 (0.11 g, 0.61 mmol) and N-benzyloxycarbonyl-glycine 11 (98.5%) (0.17 g, 0.79 mmol) in dry dichloromethane (35 cm$^3$) under an atmosphere of nitrogen at room temperature, and the reaction mixture stirred for 10 min. Bis(2-oxo-3-oxazolidinyl)phosphinic chloride (BoPCl, 97%) (0.196 g, 0.77 mmol) was added and the resultant colourless solution was stirred for 20.5 h. The solution was washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (50-80% ethyl acetate-hexane; gradient elution) yielded dipeptide 12 (0.18 g, 92%) as a colourless oil. Amide 12 was shown to exist as a 98:2 trans:cis mixture of conformers by $^{13}$C NMR analysis (the ratio was estimated from the relative intensities of the resonances at δ 20.8 and 23.5 assigned to the Proγ-C atoms of the minor and major conformers, respectively): [α]$_D$-33.0 (c 1.0 in MeOH); ν$_{max}$ (film)/cm$^{-1}$ 3406, 2952, 1732, 1651, 1521, 1434, 1373, 1329, 1310, 1284, 1257, 1220, 1195, 1172, 1135, 1107, 1082, 1052, 1029, 986, 965, 907, 876, 829, 775, 738 and 699; $\delta_H$ (300 MHz, CDCl$_3$) 1.49 (3H, s, CH$_3$), 1.77-2.11 (4H, m, Proβ-H$_2$ and Proγ-H$_2$), 3.43-3.48 (2H, m, Proδ-H$_2$), 3.61 (3H, s, OCH$_3$), 3.85-3.89 (2H, m, Glyα-H$_2$), 5.04 (2H, s, PhCH$_2$), 5.76 (1H, br s, N—H) and 7.21-7.28 (5H, s, ArH); $\delta_C$ (75 MHz, CDCl$_3$) 13.8* (CH$_3$, Proα-CH$_3$), 21.1 (CH$_3$, Proα-CH$_3$), 20.8* (CH$_2$, Proγ-C), 23.5 (CH$_2$, Proγ-C), 38.0 (CH$_2$, Proβ-C), 40.8* (CH$_2$, Proβ-C), 43.3 (CH$_2$, Glyα-C), 45.5* (CH$_2$, Glyα-C), 46.6 (CH$_2$, Proδ-C), 48.7* (CH$_2$, Proδ-C), 51.9* (CH$_3$, OCH$_3$), 52.1 (CH$_3$, OCH$_3$), 60.0* (quat., Proα-C), 66.0 (quat., Proα-C), 66.3 (CH$_2$, PhCH$_2$), 68.6* (CH$_2$, PhCH$_2$), 127.5 (CH, Ph), 127.6 (CH, Ph), 127.9* (CH, Ph), 128.1 (CH, Ph), 128.3* (CH, Ph), 136.2 (quat., Ph), 155.9 (quat., NCO$_2$), 166.0 (quat., Gly-CON), 169.4* (quat., Gly-CON) and 173.6 (quat., CO$_2$CH$_3$); m/z (EI+) 334.1535 (M$^+$. C$_{17}$H$_{22}$N$_2$O$_5$ requires 334.1529).

(8aS)-Methyl-hexahydropyrrolo[1,2-a]pyrazine-1,4-dione (Cyclic G-2MeP)

To a solution of dipeptide 12 (0.167 g, 0.51 mmol) in methanol (8.0 cm$^3$) was added 10% Pd on activated charcoal (8.1 mg, 0.076 mmol) and the vessel flushed with hydrogen gas. The resulting suspension was stirred vigorously under an atmosphere of hydrogen for 15 h. The mixture was then filtered through a Celite pad then a short plug of silica gel with methanol, and the solvent removed under reduced pressure to produce cyclic G-2MeP (83 mg, 98%) as a yellow solid: mp 133-135° C.; [α]$_D$-128.1 (c 0.52 in MeOH); $\delta_H$ (300 MHz, CDCl$_3$) 1.36 (3H, s, CH$_3$), 1.87-2.01 (3H, m, Proβ-H$_A$H$_B$ and Proγ-H$_2$), 2.07-2.21 (1H, m, Proβ-H$_A$H$_B$), 3.45-3.64 (2H, m, Proδ-H$_2$), 3.82 (1H, dd, J 17.1 and 4.1, CH$_A$H$_B$NH), 3.99 (1H, d, J 17.1, CH$_A$H$_B$NH) and 7.66 (1H, br s, N—H); $\delta_C$ (75 MHz, CDCl$_3$) 20.2 (CH$_2$, Proγ-C), 23.2 (CH$_3$, Proα-CH$_3$), 35.0 (CH$_2$, Proβ-C), 44.7 (CH$_2$, Proδ-C), 45.9 (CH$_2$, CH$_2$NH), 63.8 (quat., Proα-C), 163.3 (quat., NCO) and 173.3 (quat., CONH); m/z (EI+) 168.08986 (M$^+$. C$_8$H$_{12}$N$_2$O$_2$ requires 168.08988).

Example 2

Synthesis of (8aS)-Methyl-spiro[cyclohexane-1,3(4H)-tetrahydropyrrolo[1,2-a]pyrazine]-1,4(2H)-dione (Cyclic cyclohexyl-G-2MeP)

Scheme 2: Reagents, conditions and yields:

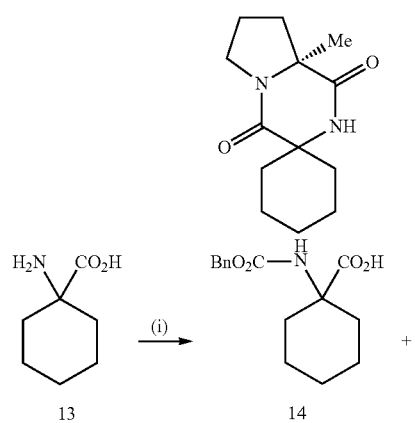

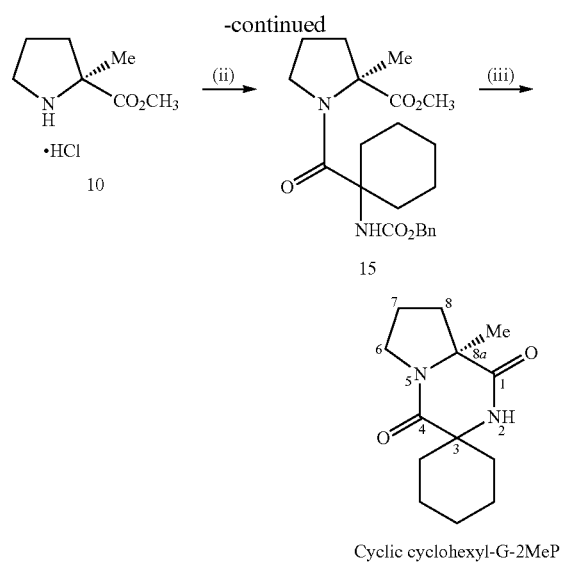

Cyclic cyclohexyl-G-2MeP (i) BnO$_2$CCl, Na$_2$CO$_3$, H$_2$O-dioxane (3:1), 19 h, 96%;
(ii) Et$_3$N, HOAt, CIP, 1,2-dichloroethane, reflux, N$_2$, 19 h (23%);
(iii) 10% Pd/C, CH$_3$OH, RT, 17 h (65%).

N-benzyloxycarbonyl-1-aminocyclohexane-1-carboxylic acid (14)

To a suspension of 1-aminocyclohexanecarboxylic acid 13 (0.72 g, 5.02 mmol) and sodium carbonate (1.6 g, 15.1 mmol) were dissolved in water-dioxane (21 cm$^3$, 3:1) was added benzyl chloroformate (0.79 cm$^3$, 5.52 mmol) was added dropwise and the solution was stirred at room temperature for 19.5 h. The aqueous layer was washed with diethyl ether (60 cm$^3$), acidified with 2 M HCl and extracted with ethyl acetate (2×60 cm$^3$). The organic layers were combined, dried (MgSO$_4$), filtered and evaporated under reduced pressure to produce a colourless oil, which solidified on standing to crude carbamate 14 (1.23 g, 88%) as a white solid: mp 152-154° C. (lit., 148-150° C.); $\delta_H$ (400 MHz, CDCl$_3$) 1.27-1.56 (3H, m, 3× cyclohexyl-H), 1.59-1.73 (3H, m, 3× cyclohexyl-H), 1.85-1.91 (2H, m, 2× cyclopentyl-H), 2.05-2.09 (2H, m, 2× cyclopentyl-H), 5.02 (1H, br s, N—H), 5.12 (2H, s, OCH$_2$Ph) and 7.27-7.36 (5H, s, Ph); $\delta_C$ (100 MHz, CDCl$_3$) 21.1 (CH$_2$, 2× cyclohexyl-C), 25.1 (CH$_2$, 2× cyclohexyl-C), 32.3 (CH$_2$, cyclohexyl-C), 59.0 (quat., 1-C), 67.1 (CH$_2$, OCH$_2$Ph), 128.1 (CH, Ph), 128.2 (CH, Ph), 128.5 (CH, Ph), 136.1 (quat., Ph), 155.7 (quat., NCO$_2$) and 178.7 (quat., CO$_2$H).

Methyl-N-benzyloxycarbonyl-cyclohexyl-glycyl-L-2-methylprolinate (15)

Dry triethylamine (0.21 cm$^3$, 1.5 mmol) was added dropwise to a solution of hydrochloride 10 (84.0 mg, 0.47 mmol), carboxylic acid 14 (0.17 g, 0.61 mmol) and 1-hydroxy-7-azabenzotriazole (16 mg, 0.12 mmol) in dry 1,2-dichloroethane (26 cm$^3$) under an atmosphere of nitrogen at room temperature, and the reaction mixture stirred for 10 min. 2-Chloro-1,3-dimethylimidazolidinium hexafluorophosphate (0.13 g, 0.47 mmol) was added and the resultant solution heated under reflux for 21 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (40-50% ethyl acetate-hexane; gradient elution) yielded amide 15 (16 mg, 9%) as a white solid. Amide 15 was shown to exist as a 11:1 trans:cis mixture of conformers by $^{13}$C NMR analysis (the ratio was estimated from the relative intensities of the resonances at δ 41.3 and 48.2 assigned to the Proδ-C atoms of the minor and major conformers, respectively): mp 219-222° C.; [α]$_D$-44.9 (c 1.31 in CH$_2$Cl$_2$); ν$_{max}$ (film)/cm$^{-1}$ 3239, 2927, 1736, 1707, 1617, 1530, 1450, 1403, 1371, 1281, 1241, 1208, 1194, 1165, 1150, 1132, 1089, 1071, 1028, 984, 912, 796, 749, 739 and 699; δ$_H$ (400 MHz, CDCl$_3$) 1.24-2.10 (17H, m, Proα-CH$_3$, Proβ-H$_2$, Proγ-H$_2$ and 5× cyclohexyl-H$_2$), 3.25-3.48 (1H, br m, Proδ-H$_A$H$_B$), 3.61-3.87 (4H, br m, OCH$_3$ and Proδ-H$_A$H$_B$), 4.92-5.19 (3H, m, N—H and OCH$_2$Ph) and 7.35-7.37 (5H, s, Ph); δ$_C$ (100 MHz, CDCl$_3$) 21.26 (CH$_2$, cyclohexyl-C), 21.33 (CH$_2$, cyclohexyl-C), 21.7 (CH$_3$, Proα-CH$_3$), 24.8 (CH$_2$, cyclohexyl-C), 25:0 (CH$_2$, Proγ-C), 29.4* (CH$_2$, cyclohexyl-C), 29.7* (CH$_2$, cyclohexyl-C), 31.1 (CH$_2$, cyclohexyl-C), 31.6 (CH$_2$, cyclohexyl-C), 31.9* (CH$_2$, cyclohexyl-C), 32.2* (CH$_2$, cyclohexyl-C), 32.8* (CH$_2$, cyclohexyl-C), 37.3 (CH$_2$, Proβ-C), 41.4* (CH$_2$, Proδ-C), 48.2 (CH$_2$, Proδ-C), 52.1 (CH$_3$, OCH$_3$), 59.1 (quat., Glyα-C), 66.7 (CH$_2$, OCH$_2$Ph), 67.3* (CH$_2$, OCH$_2$Ph), 67.4 (quat., Proα-C), 128.0* (CH, Ph), 128.1* (CH, Ph), 128.3 (CH, Ph), 128.5 (CH, Ph), 128.7 (CH, Ph), 136.6 (quat., Ph), 153.7 (quat., NCO$_2$), 171.0 (quat., Gly-CO) and 174.8 (quat., CO$_2$CH$_3$); m/z (EI+) 402.2151 (M$^+$. C$_{22}$H$_{30}$N$_2$O$_5$ requires 402.2155).

(8aS)-Methyl-spiro[cyclohexane-1,3(4H)-tetrahydropyrrolo[1,2-a]pyrazine]-1,4(2H)-dione (Cyclic cyclohexyl-G-2MeP)

To a solution of amide 15 (40 mg, 0.01 mmol) in methanol (3.3 cm$^3$) was added 10% Pd on activated charcoal (1.6 mg, 0.015 mmol) and the vessel flushed with hydrogen gas. The resulting suspension was stirred vigorously under an atmosphere of hydrogen for 61.5 h, then filtered through a Celite™ pad with methanol (15 cm$^3$). The filtrate was concentrated to dryness under reduced pressure to produce a yellow semi-solid which was purified by reverse-phase C18 flash column chromatography (0-10% CH$_3$CN/H$_2$O; gradient elution) to produce cyclic cyclohexyl-G-2MeP (19 mg, 81%) as a white solid: mp 174-177° C.; [α]$_D$-63.8 (c 1.13 in CH$_2$Cl$_2$); ν$_{max}$ (film)/cm$^{-1}$ 3215, 2925, 2854, 1667, 1646, 1463, 1427, 1276, 1232, 1171, 1085, 1014, 900, 868, 818, 783, 726 and 715; δ$_H$ (400 MHz, CDCl$_3$) 1.31-1.89 (12H, m, 9× cyclohexyl-H and 8a-CH$_3$), 194-2.15 (4H, m, 7-H$_2$ and 8-H$_2$), 2.26 (1H, td, J 13.7 and 4.5, 1× cyclohexyl-H), 3.44-3.51 (1H, m, 6-H$_A$H$_B$), 3.79-3.86 (1H, m, 6-H$_A$H$_B$) and 6.40 (1H, br s, N—H); δ$_C$ (100 MHz, CDCl$_3$) 19.5 (CH$_2$, 7-C), 20.6 (CH$_2$, cyclohexyl-C), 20.8 (CH$_2$, cyclohexyl-C), 24.5 (CH$_2$, cyclohexyl-C), 25.0 (CH$_3$, 8a-CH$_3$), 33.7 (CH$_2$, cyclohexyl-C), 36.3 (CH$_2$, 8-C), 36.5 (CH$_2$, cyclohexyl-C), 44.7 (CH$_2$, 6-C), 59.5 (quat., 8a-C), 64.0 (quat., 3-C), 168.1 (quat., 4-C) and 171.6 (quat., 1-C); m/z (EI+) 236.15246 (M$^+$. C$_{13}$H$_{20}$N$_2$O$_2$ requires 236.15248).

Example 3

Synthesis of (8aS)-Allyl-hexahydropyrrolo[1,2-a]pyrazine-1,4-dione (Cyclic G-2AllylP)

Scheme 3: Reagents, conditions and yields:

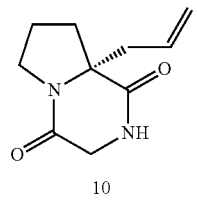

10

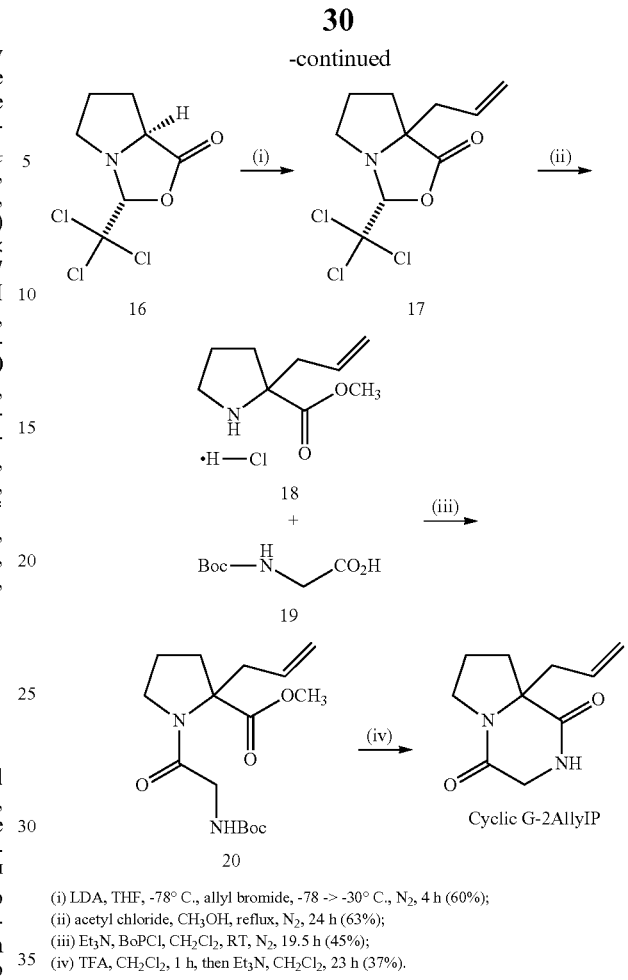

(i) LDA, THF, -78° C., allyl bromide, -78 -> -30° C., N$_2$, 4 h (60%);
(ii) acetyl chloride, CH$_3$OH, reflux, N$_2$, 24 h (63%);
(iii) Et$_3$N, BoPCl, CH$_2$Cl$_2$, RT, N$_2$, 19.5 h (45%);
(iv) TFA, CH$_2$Cl$_2$, 1 h, then Et$_3$N, CH$_2$Cl$_2$, 23 h (37%).

(2R,5S)-4-Allyl-2-trichloromethyl-1-aza-3-oxabicyclo[3.3.0]octan-4-one 17 n-BuLi (1.31 M, 9.93 cm$^3$, 13.0 mmol) was added dropwise to a stirred solution of diisopropylamine (1.82 cm$^3$, 13.0 mmol) in dry tetrahydrofuran (20 cm$^3$) at −78° C. under an atmosphere of nitrogen. The solution was stirred for 5 min, warmed to 0° C., stirred for 15 min then added dropwise to a solution of pro-oxazolidinone 16 (2.12 g, 8.68 mmol) in dry tetrahydrofuran (40 cm$^3$) at −78° C. over 20 min and the reaction mixture was stirred for a further 30 min then allyl bromide (2.25 cm$^3$, 26.0 mmol) was added dropwise over 5 min. The solution was warmed slowly to −30° C. over 4 h, quenched with H$_2$O (30 cm$^3$) and the mixture warmed to room temperature and extracted with chloroform (3×80 cm$^3$). The combined organic extracts were dried (MgSO$_4$), filtered and evaporated to dryness in vacuo to produce a dark brown semi-solid which was purified by flash column chromatography (10-20% ethyl acetate-hexane; gradient elution) to produce oxazolidinone 17 (1.48 g, 60%) as an orange oil which solidified at 0° C., for which the nmr data were in agreement with that reported in the literature: δ$_H$ (400 MHz, CDCl$_3$) 1.58-1.92 (2H, m, Proγ-H$_2$), 1.96-2.14 (2H, m, Proβ-H$_2$), 2.50-2.63 (2H, m, Proδ-H$_2$), 3.12-3.23 (2H, m, CH$_2$—CH=CH$_2$), 4.97 (1H, s, NCH), 5.13-5.18 (2H, m, CH=CH$_2$) and 5.82-5.92 (1H, m, CH=CH$_2$); δ$_C$ (100 MHz, CDCl$_3$) 25.1 (CH$_2$, Proγ-C), 35.1 (CH$_2$, Proβ-C), 41.5 (CH$_2$, Proδ-C), 58.3 (CH$_2$, CH$_2$CH=CH$_2$), 71.2 (quat., Proα-C), 100.4 (quat., CCl$_3$), 102.3 (CH, NCH), 119.8 (CH$_2$, CH$_2$CH=CH$_2$), 131.9 (CH, CH$_2$CH=CH$_2$) and 176.1 (quat., C=O); m/z (CI+) 284.0009 [(M+H)$^+$. C$_{10}$H$_{13}$$^{35}$Cl$_3$NO$_2$ requires 284.0012], 285.9980 [(M+H)$^+$. C$_{10}$H$_{13}$$^{35}$Cl$_2$$^{37}$ClNO$_2$ requires 285.9982], 287.9951 [(M+H)$^+$. C$_{10}$H$_{13}$$^{35}$Cl$^{37}$Cl$_2$NO$_2$ requires 287.9953] and 289.9932 [(M+H)$^+$. C$_{10}$H$_{13}$$^{37}$Cl$_3$NO$_2$ requires 289.9923].

Methyl L-2-allylprolinate hydrochloride 18

An ice-cooled solution of oxazolidinone 17 (0.64 g, 2.24 mmol) in dry methanol (15 cm$^3$) was treated dropwise with a solution of acetyl chloride (0.36 cm$^3$, 5.0 mmol) in methanol (5 cm$^3$). The solution was heated under reflux for 24 h, then cooled and the solvent removed under reduced pressure. The resultant brown oil was dissolved in toluene (40 cm$^3$) and concentrated to dryness to remove residual thionyl chloride and methanol, then purified by flash column chromatography (5-10% CH$_3$OH—CH$_2$Cl$_2$; gradient elution) to afford hydrochloride 18 (0.29 g, 63%) as a green solid for which the NMR data were in agreement with that reported in the literature: δ$_H$ (300 MHz, CDCl$_3$) 1.72-2.25 (3H, m, Proβ-H$_A$H$_B$ and Proγ-H$_2$), 2.32-2.52 (1H, m, Proβ-H$_A$H$_B$), 2.72-3.10 (2H, m, Proδ-H$_2$), 3.31-3.78 (2H, m, CH$_2$CH=CH$_2$), 3.84 (3H, s, CO$_2$CH$_3$), 5.20-5.33 (2H, m, CH=CH$_2$), 5.75-5.98 (1H, m, CH=CH$_2$) and 8.06 (1H, br s, N—H); m/z (CI+) 170.1183 [(M+H)$^+$. C$_9$H$_{16}$NO$_2$ requires 170.1181].

Methyl-N-tert-butyloxycarbonyl-glycyl-L-2-allylprolinate 20

Dry triethylamine (0.28 cm$^3$, 2.02 mmol) was added dropwise to a solution of hydrochloride 18 (0.13 g, 0.63 mmol) and N-tert-butyloxycarbonyl-glycine 19 (0.14 g, 0.82 mmol) in dry dichloromethane (35 cm$^3$) under an atmosphere of nitrogen at room temperature, and the reaction mixture was stirred for 10 min. Bis(2-oxo-3-oxazolidinyl)phosphinic chloride (BoPCl, 97%) (0.20 g, 0.80 mmol) was added and the solution stirred for 19.5 h, then washed successively with 10% aqueous, hydrochloric acid (35 cm$^3$) and saturated aqueous sodium hydrogen carbonate (35 cm$^3$), dried (MgSO$_4$), filtered and evaporated to dryness in vacuo. Purification of the resultant residue by flash column chromatography (40% ethyl acetate-hexane) yielded dipeptide 20 (0.09 g, 45%) as a light yellow oil: [α]$_D$+33.8 (c 0.83 in CH$_2$Cl$_2$); ν$_{max}$ (film)/cm$^{-1}$ 3419, 3075, 2977, 2930, 2874, 1739, 1715, 1656, 1499, 1434, 1392, 1366, 1332, 1268, 1248, 1212, 1168, 1122, 1051, 1026, 1003, 943, 919, 867, 830, 779, 739, 699 and 679; δ$_H$ (300 MHz, CDCl$_3$) 1.42 [9H, s, C(CH$_3$)$_3$], 1.93-2.08 (4H, m, Proβ-H$_2$ and Proγ-H$_2$), 2.59-2.67 (1H, m, CH$_A$H$_B$CH=CH$_2$), 3.09-3.16 (1H, m, CH$_A$H$_B$CH=CH$_2$), 3.35-3.44 (1H, m, Proδ-H$_A$H$_B$), 3.56-3.62 (1H, m, Proδ-H$_A$H$_B$), 3.70 (3H, s, OCH$_3$), 3.89 (2H, d, J 4.2, Glyα-H$_2$), 5.06-5.11 (2H, m, CH=CH$_2$), 5.42 (1H, br s, Gly-NH) and 5.58-5.72 (1H, m, CH=CH$_2$); δ$_C$ (75 MHz, CDCl$_3$) 23.7 (CH$_2$, Proγ-C), 28.3 [CH$_3$, C(CH$_3$)$_3$], 35.0 (CH$_2$, Proβ-C), 37.6 (CH$_2$, CH$_2$CH=CH$_2$), 43.3 (CH$_2$, Glyα-C), 47.5 (CH$_2$, Proδ-C), 52.5 (CH$_3$, OCH$_3$), 68.8 (quat., Proα-C), 79.5 [quat., C(CH$_3$)$_3$], 119.4 (CH$_2$, CH=CH$_2$), 132.9 (CH, CH=CH$_2$), 155.7 (quat., NCO$_2$), 166.9 (quat., Gly-CON) and 173.8 (quat., CO$_2$CH$_3$); m/z (EI+) 326.1845 (M$^+$. C$_{16}$H$_{26}$N$_2$O$_5$ requires 326.1842).

(8aS)-Allyl-hexahydropyrrolo[1,2-a]pyrazine-1,4-dione (Cyclic G-2AllyIP)

To a solution of dipeptide 20 (0.09 g, 028 mmol) in dichloromethane (9 cm$^3$) at room temperature was added trifluoroacetic acid (1 cm$^3$, 0.013 mmol) dropwise and the reaction mixture was stirred for 1 h under an atmosphere of nitrogen. The solution was evaporated under reduced pressure to give a colorless oil which was dissolved in dichloromethane (10 cm$^3$), dry triethylamine (0.096 cm$^3$, 0.69 mmol) was added and the reaction mixture stirred for 4.5 h, after which further triethylamine (0.096 cm$^3$, 0.69 mmol) was added. The reaction mixture was stirred overnight, concentrated to dryness to give a green oil which was purified by flash column chromatography (10% CH$_3$OH—CH$_2$Cl$_2$) to produce cyclic G-2AllyIP (20 mg, 37%) as an off-white solid: mp 106-109° C.; [α]$_D$-102.7 (c 0.95 in CH$_2$Cl$_2$); ν$_{max}$ (CH$_2$Cl$_2$)/cm$^{-1}$ 3456, 3226, 2920, 1666, 1454, 1325, 1306, 1299, 1210, 1133, 1109, 1028, 1010, 949, 928, 882, 793, 761 and 733; δ$_H$ (400 MHz, CDCl$_3$) 1.92-2.01 (2H, m, Proγ-H$_2$), 2.09-2.16 (2H, m, Proβ-H$_2$), 2.39-2.56 (2H, m, CH$_2$CH$_2$=CH$_2$), 3.46-3.53 (1H, m, Proδ-H$_A$H$_B$), 3.78-3.87 (2H, m, Proδ-H$_A$H$_B$ and Glyα-H$_A$H$_B$), 4.09 (1H, d, J 17.2, Glyα-H$_A$H$_B$), 5.16-5.20 (2H, m, CH=CH$_2$), 5.73-5.84 (1H, m, CH=CH$_2$) and 7.17 (1H, br s, N—H); δ$_C$ (100 MHz, CDCl$_3$) 20.1 (CH$_2$, Proγ-C), 34.1 (CH$_2$, Proβ-C), 41.7 (CH$_2$, CH$_2$CH$_2$=CH$_2$), 44.9 (CH$_2$, Proδ-C), 46.4 (CH$_2$, Glyα-C), 67.2 (quat., Proα-C), 120.9 (CH$_2$, CH=CH$_2$), 131.0 (CH, CH=CH$_2$), 163.4 (quat., NCO) and 171.7 (quat., CONH); m/z (EI+) 195.1132 (M$^+$. C$_{10}$H$_{15}$N$_2$O$_2$ requires 195.1134).

Example 4

Synthesis of (8aS)-Methyl-spiro[cyclopentane-1,3 (4H)-tetrahydropyrrolo[1,2-a]pyrazine]-1,4(2H)-dione (Cyclic Cyclopentyl-G-2MeP)

Scheme 4: Reagents, conditions and yields:

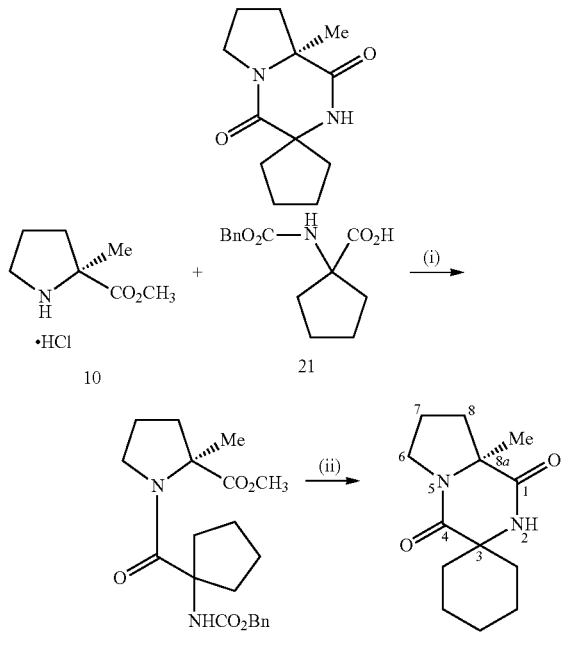

22                       Cyclic cyclohexyl-G-2MeP (i) Et$_3$N, HOAt, CIP, 1,2-dichloroethane, 83° C., N$_2$, 19 h (23%);
(ii) 10% Pd/C, CH$_3$OH, RT, 17 h (65%).

N-Benzyloxycarbonyl-1-aminocyclopentane-1-carboxylic acid 21

A solution of benzyl chloroformate (0.290 g, 1.1 mmol) in dioxane (2.5 cm$^3$) was added dropwise to a solution of 1-aminocyclopentanecarboxylic acid (Fluka) (0.2 g, 1.54 mmol) and sodium carbonate (0.490 g, 4.64 mmol) in water (5 cm$^3$) at 0° C. Stirring was continued at room temperature overnight and the reaction mixture washed with ether. The aqueous layer was acidified with 2M hydrochloric acid, extracted with ethyl acetate, dried (Na$_2$SO$_4$), filtered and the solvent removed to afford carbamate 21 (0.253 g, 62%) as an oil which solidified on standing. Carbamate 21 was shown to be a 70:30 mixture of conformers by $^1$H NMR analysis (the ratio was estimated from the integration of the resonances at δ 5.31 and 7.29-7.40, assigned to the N—H protons of the major and minor conformers, respectively): mp 70-80° C. (lit.[1] 82-86° C., ethyl acetate, petroleum ether); $δ_H$ (400 MHz; CDCl$_3$; Me$_4$Si) 1.83 (4H, br s, 2× cyclopentyl-H$_2$), 2.04 (2H, br s, cyclopentyl-H$_2$), 2.20-2.40 (2H, m, cyclopentyl-H$_2$), 5.13 (2H, br s, OCH$_2$Ph), 5.31 (0.7H, br s, N—H) and 7.29-7.40 (5.3H, m, Ph and N—H*); $δ_C$ (100 MHz; CDCl$_3$) 24.6 (CH$_2$, cyclopentyl-C), 37.5 (CH$_2$, cyclopentyl-C), 66.0 (quat., cyclopentyl-C), 66.8 (CH$_2$, OCH$_2$Ph), 128.0 (CH, Ph), 128.1 (CH, Ph), 128.4 (CH, Ph), 136.1 (quat, Ph), 155.8 (quat., NCO$_2$) and 179.5 (quat., CO$_2$H).

Methyl N-benzyloxycarbonyl cyclopentyl-glycyl-L-2-methylprolinate 22

Dry triethylamine (0.19 cm$^3$, 1.4 mmol) was added dropwise to a solution of hydrochloride 10 (78 mg, 0.43 mmol), carboxylic acid 21 (0.15 g, 0.56 mmol) and 1-hydroxy-7-azabenzotriazole (Acros) (15 mg, 0.11 mmol) in dry 1,2-dichloroethane (24 cm$^3$) under an atmosphere of nitrogen at room temperature, and the reaction mixture stirred for 10 min. 2-Chloro-1,3-dimethylimidazolidinium hexafluorophosphate (CIP) (Aldrich) (0.12 g, 0.43 mmol) was added and the resultant solution heated under reflux for 19 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (60% ethyl acetate-hexane) yielded amide 22 (39 mg, 23%) as a white solid. Amide 22 was shown to exist as a 3:1 trans:cis mixture of carbamate conformers by $^{13}$C NMR analysis (the ratio was estimated from the relative intensities of the resonances at δ 154.1 and 155.7 assigned to the carbamate carbonyl-C atoms of the major and minor conformers, respectively): mp 200-203° C.; [α]$_D$-54.5 (c 1.52 in CH$_2$Cl$_2$); $ν_{max}$ (film)/cm$^{-1}$ 3432, 3239, 3042, 2953, 1736, 1712, 1627, 1540, 1455, 1417, 1439, 1374, 1282, 1256, 1216, 1194, 1171, 1156, 1136, 1100, 1081, 1042, 1020, 107, 953, 917, 876, 756 and 701; $δ_H$(400 MHz, CDCl$_3$) 1.33-1.53 (3H, br m, Proα-CH$_3$), 1.62-2.20 (11H, m, Proβ-H$_2$, Proγ-H$_2$ and 7× cyclopentyl-H), 2.59-2.71 (1H, br m, 1× cyclopentyl-H), 3.31-3.42 (1H, br m, Proδ-H$_A$H$_B$), 3.58-3.79 (4H, br m, OCH$_3$ and Proδ-H$_A$H$_B$), 4.92-5.17 (3H, m, N—H and OCH$_2$Ph) and 7.27-7.42 (5H, s, Ph); $δ_C$ (100 MHz, CDCl$_3$) 21.7 (CH$_3$, Proα-CH$_3$), 24.1* (CH$_2$, cyclopentyl-C), 24.2 (CH$_2$, cyclopentyl-C), 24.4 (CH$_2$, Proγ-C), 24.5 (CH$_2$, cyclopentyl-C), 36.4 (CH$_2$, cyclopentyl-C), 37.1 (CH$_2$, cyclopentyl-C), 37.2* (CH$_2$, cyclopentyl-C), 37.7 (CH$_2$, Proβ-C), 38.2* (CH$_2$, cyclopentyl-C), 48.5 (CH$_2$, Proδ-C), 52.1 (CH$_3$, OCH$_3$), 66.6 (CH$_2$, OCH$_2$Ph), 66.9 (quat., Proα-C), 67.2 (quat., Glyα-C), 127.8 (CH, Ph), 128.2 (CH, Ph), 128.4 (CH, Ph), 136.6 (quat., Ph), 154.1 (quat., NCO$_2$), 155.7* (quat., NCO$_2$), 170.5 (quat., Gly-CO) and 174.7 (quat., CO$_2$CH$_3$); m/z (EI+) 388.1991 (M$^+$. C$_{21}$H$_{28}$N$_2$O$_5$ requires 388.1998).

* denotes resonance asigned to minor conformer.

(8aS)-Methyl-spiro[cyclopentane-1,3 (4H)-tetrahydropyrrolo [1,2-a]pyrazine]-1,4(2H)-dione (Cyclic cyclopentyl-G-2MeP)

To a solution of amide 22 (54 mg, 0.14 mmol) in methanol (4.6 cm$^3$) was added 10% Pd on activated charcoal (2.2 mg, 0.021 mmol) and the vessel flushed with hydrogen gas. The resulting suspension was stirred vigorously under an atmosphere of hydrogen for 17 h, then filtered through a Celite™ pad with methanol (15 cm$^3$). The filtrate was concentrated to dryness under reduced pressure to give a yellow semi-solid which was purified by reverse-phase C18 flash column chromatography (0-10% CH$_3$CN/H$_2$O; gradient elution) to afford cyclic cyclopentyl-G-2MeP (20 mg, 65%) as a yellow solid: mp 160-163° C.; [α]$_D$-97.9 (c 1.61 in CH$_2$Cl$_2$); $ν_{max}$ (film)/cm$^{-1}$ 3429, 2956, 2928, 2856, 1667, 1643, 1463, 1432, 1373, 1339, 1254, 1224, 1175, 1086, 1048, 976, 835, 774 and 730; $δ_H$ (300 MHz, CDCl$_3$) 1.47 (3H, br s, 8a-CH$_3$), 1.56-2.19 (11H, m, 8-H$_2$, 7-H$_2$ and 7× cyclopentyl), 2.58-2.67 (1H, br m, 1× cyclopentyl), 3.48-3.56 (1H, m, 6-H$_A$H$_B$), 3.72-3.82 (1H, m, 6-H$_A$H$_B$) and 6.56 (1H, br s, N—H); $δ_C$ (75 MHz, CDCl$_3$) 19.9 (CH$_2$, 7-C), 24.6 (CH$_2$, cyclopentyl), 24.92 (CH$_3$, 8a-CH$_3$), 24.93 (CH$_2$, cyclopentyl), 36.0 (CH$_2$, 8-C), 38.7 (CH$_2$, cyclopentyl), 41.9 (CH$_2$, cyclopentyl), 44.8 (CH$_2$, 6-C), 64.3 (quat., 8a-C), 66.8 (quat., 3-C), 168.3 (quat., 4-C) and 172.2 (quat., 1-C); m/z (EI+) 222.1369 (M$^+$. C$_{12}$H$_{18}$N$_2$O$_2$ requires 222.1368).

In Vitro and In Vivo Testing

The following pharmacological studies demonstrate neuroprotective features of this invention. They are not intended to be limiting, and other compositions and methods of this invention can be developed without undue experimentation. All of those compositions and methods are considered to be part of this invention. All the following experiments were carried out using protocols developed under guidelines approved by the University of Auckland Animal Ethics Committee.

Example 5

Effects of Cyclic G-2AllylP and Cyclic cyclopentyl-G-2MeP on Cerebellar Cell Explants To determine the effects of cG-2AllylP and cyclic cyclopentyl-G-2MeP on neuronal cells in vitro, a series of studies was carried out using cerebellar explants from adult rats. In vitro systems are suitable for studying neuronal proliferation, neurite growth, formation of nerve bundles and effects of toxins on neural cells, effects that parallel effects observed in vivo. Thus, results of studies using in vitro cerebellar explants are predictive of effects of interventions in vivo.

In a first series of studies, effects of glutamate on cerebellar explants were determined. At physiological concentrations, glutamate is a neurotransmitter in the CNS of mammals, including humans. However, at sufficiently high concentrations, glutamate is neurotoxic, resulting in neuronal cell death. Because glutamate is a naturally occurring neurotransmitter in the CNS of mammals, including humans, and because glutamate neurotoxicity is recognized in the art as reflective of neurotoxicity in general, and including cell death and degeneration, it is a valuable tool useful for identifying and characterizing agents effective in treatment of neurodegeneration and neural cell death.

Materials and Methods

Cover slips were placed into a large Petri dish and washed in 70% alcohol for 5 minutes, then washed with Millipore $H_2O$. The cover slips were air dried, and coated with Poly-D-Lysine (1 mg/ml stock solution in PBS, 90-100 µl) for 2 hours at 34° C.

Extraction of Cerebellar Tissue

Postnatal day 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 µl 65% stock D (+)glucose/1 ml PBS) in a large Petri dish, chopped up into smaller sections and triturated with a 1 ml insulin syringe via a 23 G (0.4 mm) needle, and then squirted back into the glucose solution in the large Petri dish. The tissue was sieved through (125 µm pore size gauze) and centrifuged (2 minutes at 60 g) twice to exchange the medium into serum-free BSA-supplemented START V medium (Biochrom, Germany). The second centrifugation step was done with 1 ml of START V medium. The microexplants were reconstituted into 500 µl of START V medium and put on ice.

Cultivation of Cerebellar Cells

Two hours after PDL-coating, the slides were washed with Millipore $H_2O$ and air dried. Each slide was placed into a small Petri dish (diameter: 35 mm) and 40 µl of START V/cell suspension was added. The tissue was incubated for 2 hours at 34° C. (settlement period). START V-medium (1 ml) was then added to the Petri dish and cultivated at 34° C. in the presence of 5% $CO_2$ in air at 100% humidity for 48 hours.

Drug Application

For the study, certain explant cultures were exposed to vehicle (PBS) only. In the first study (Study 1) 10 µl of toxin 1 (L-glutamate-100 mM in Millipore water; final concentration: 1 mM) and 10 µl of toxin 2 (3-nitropropionic acid-50 mM-pH 7-in Millipore water, final concentration: 0.5 mM) was applied simultaneously with the drug to be tested (10 mM stock solution prepared in PBS and diluted to final concentrations between 1-100 nM). In each case, the drugs were left in contact with the explants for the duration of the study.

Methods for Determining Drug Effects

After explants were exposed to drugs for the study period, cells were then rinsed in PBS and then fixed in increasing concentrations of paraformaldehyde (500 µl of 0.4% PFA was applied; then 1.2% PFA; then 3% PFA and finally 4% PFA (each fixation step: 2-3 minutes). Finally, the microexplants were rinsed in PBS.

Neurons in the explants were then evaluated for morphology (presence of neurites) and counted as live cells per microscopic field. Four fields displaying highest cell density were counted per cover slip and the data presented as mean±standard error of the mean (SEM); n=4 each. Statistical significance was evaluated by using the non-paired Student's t-test.

Results

Cyclic G-2-AllylP

The results of the study are shown in FIG. 1. Glutamate treatment (1 mM; filled bar) resulted in about an 85% loss of cerebellar neurons having neurites compared to vehicle-treated controls (open bar). In contrast, cG-2AllylP significantly increased the numbers of cells having neurites in a dose-dependent manner when administered simultaneously with glutamate (shaded bars). Treatment with low doses of cG-2AllylP (100 pm to 10 nm) showed a significant decrease in glutamate-induced neurotoxicity.

Cyclic cyclopentyl-G-2MeP

Figure 2:
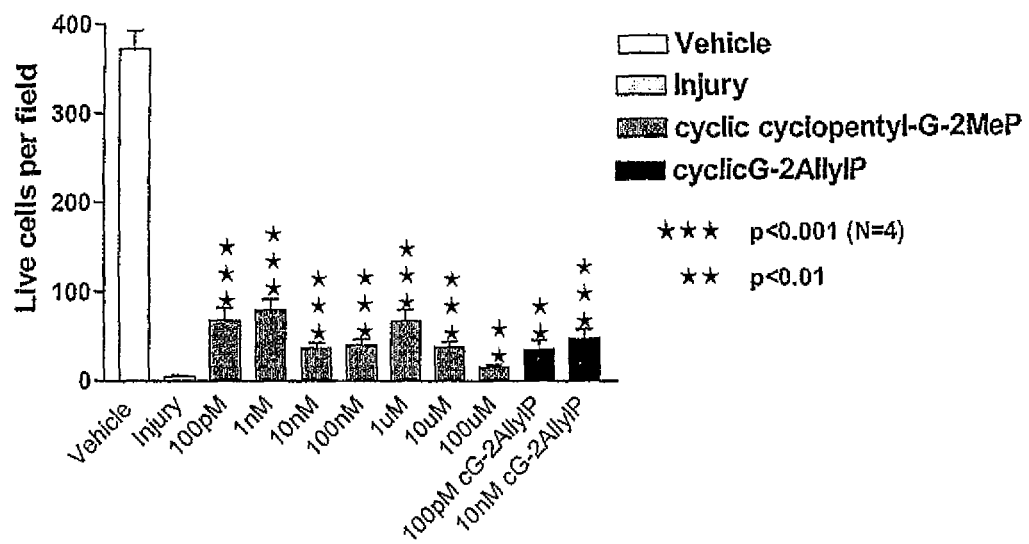
FIG. 2 is a graph showing effects of cyclic cyclopentylG-2MeP on neuronal survival in animals following excitotoxic oxidative stress.

The results of the study are shown in FIG. 2. Cyclic cyclopentyl-G-2MeP significantly increased the number of cells having neurites when simultaneously administered with glutamate (light shaded bars). Treatment with low doses of cyclic cyclopentyl-G-2MeP showed a significant decrease in glutamate-induced neurotoxicity.

Conclusions

Both cG-2AllylP and cyclic cyclopentyl-G-2MeP independently decreased or prevented glutamate-induced neurotoxicity, indicating that both drugs are neuroprotective and can be used to inhibit neuronal degeneration or cell death.

Example 6

Effects of cG-2AllylP on Hypoxic-Ischemic Injury I

Materials and Methods

To determine whether cG-2AllylP might prevent neuronal injury in response to stroke, cardiac arterial bypass graft surgery (CABG) or other hypoxic insults, a series of studies were carried out in rats that had been exposed to hypoxic-ischemic injury (HI). Adult rats (Wistar, 280-310 g, male) were used. The modified Levine model preparation and experimental procedures were used (Rice et al, 1981, *Ann. Neural.*: 9: 131-141; Guan et al J., 1993, *Cereb. Blood Flow Metab.*: 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.5 mm to the right of the mid-line and 7.5 mm anterior to the interaural zero plane under halothane anaesthesia. The right carotid artery was double ligated two days after the cannulation. After 1 hour recovery from the anaesthesia, each of the rats were placed in an incubator where the humidity (90±5%) and temperature (31°±0.5° C.) were controlled for another hour, then exposed to hypoxia (6% oxygen) for 10 min, The animals were kept in the incubator for an additional 2 hours before treatment.

Nine pairs of rats were treated intracerebral ventricularly (icy) with either cG-2AllylP (2 ng) or its vehicle (normal saline) 2 hours after hypoxic-ischemic insult. Rats in each group were simultaneously infused with cG-2AllylP or its vehicle under light anaesthesia (1.5% halothane) 2 hours after the insult. A total volume of 20 µl was infused (icy) over 20 minutes by a micro-infusion pump.

Histological examination was performed on rats 5 days after the hypoxic-ischemic injury. The rats were killed with an overdose of sodium pentobarbital and were perfused transcardially with normal saline followed by 10% formalin. The brains were kept in the same fixative for a minimum of 2 days before being processed using a standard paraffin imbedding procedure.

Coronal sections 8 µm in thickness were cut from the striatum, cerebral cortex and hippocampus and were stained with thionin and acid fuchsin. The histological outcome was assessed at three levels: (1) the mid level of the striatum, (2) where the completed hippocampus first appeared and (3) the level where the ventral horn of the hippocampus just appears. The severity of tissue damage was scored in the striatum, cortex and the CA1-2, CA3, CA4 and dentate gyrus of the hippocampus. Tissue damage was identified as neuronal loss (acidophilic (red) cytoplasm and contracted nuclei), pan-necrosis and cellular reactions. Tissue damage was scored using the following scoring system: 0: tissue showed no tissue damage, 1: <5% tissue was damaged, 2: <50% tissue was damaged, 3: >50% tissue was damaged and 4: >95% tissue was damaged.

Results and Conclusion

Figure 3:
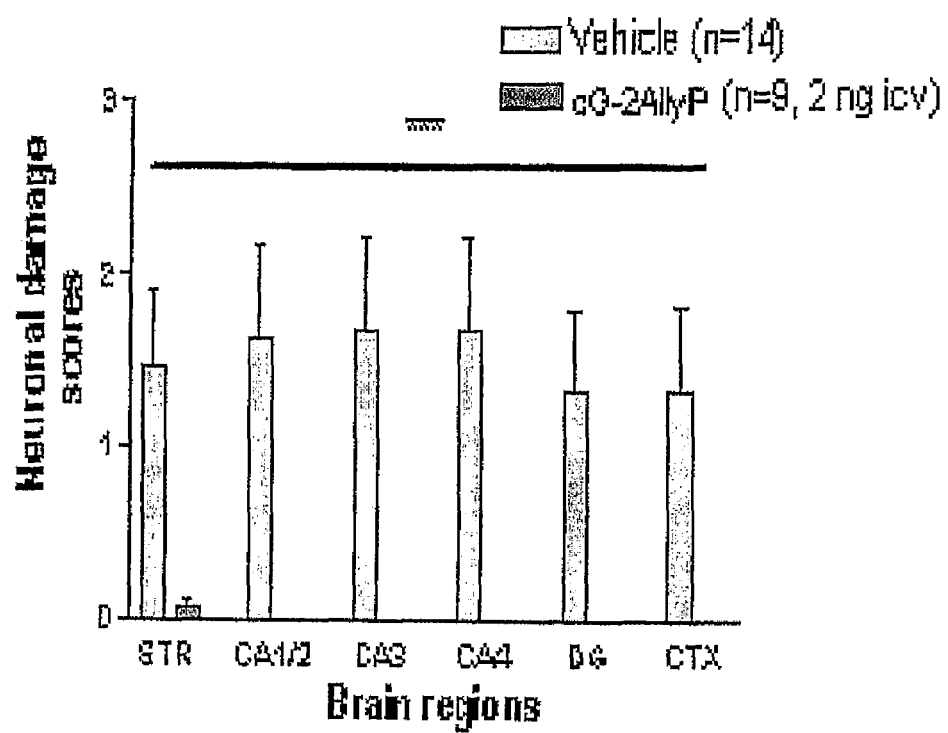
FIG. 3 is a graph showing the neuroprotective effects of cyclic G-2allylP in animals subjected to global brain ischaemia.

The results of this study are shown in FIG. 3. FIG. 3 shows that hypoxic-ischemic injury (left bars of each set) resulted in significant damage scores in each of the areas of the brain studied. FIG. 3 also shows that central administration of a relatively low dose of cG-2AllylP (right bars of each set; 2 ng) significantly reduced the tissue damage in each brain region examined compared to the vehicle treated group ($p<0.001$).

It can be seen that cG-2AllylP can be neuroprotective against neural damage caused by hypoxic-ischemic injury, even when administered after hypoxic-ischemic injury. This surprising finding indicates that cG-2AllylP is a useful agent to treat a variety of conditions characterized by neural degeneration or cell death.

Example 7

Effects of cG-2 AllylP on Hypoxic-Ischemic Injury II

Materials and Methods

Materials and methods described in Example 6 were used and the number of treatment groups was increased. Rats were divided into 5 treatment groups treated intracerebral ventricularly (icv) with one of 4 doses of cG-2AllylP or with its vehicle (normal saline) 2 hours after hypoxic-ischemic insult (1: n=10, 2 ng; 2: n=9, 4 ng; 3: n=9, 20 ng; 4: n=10, 100 ng; and 5: n=9, vehicle).

Figure 4:
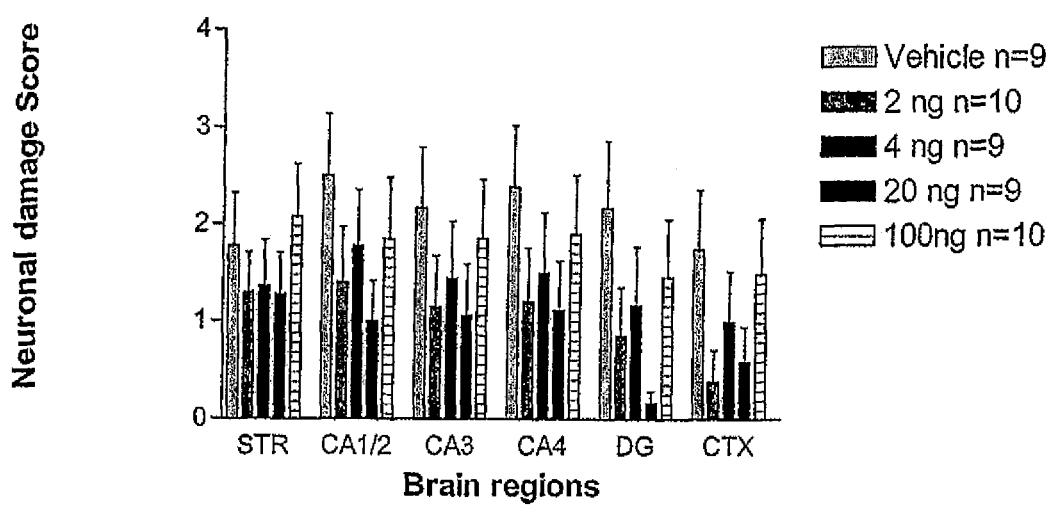
FIG. 4 is a graph showing effects of different doses of cyclic G-2allylP on neuroprotection in animals subjected to global brain ischaemia.

FIG. 4 shows hypoxia alone (vehicle) produces neuronal damage scores in all areas of the brain studied. In animals treated with cG-2allylP, hypoxia had less effect, even though the agent was administered after the hypoxic/ischemic injury. The neuroprotective effect was observed for all doses of cG-2allylP, except for the highest dose (100 ng) administered to the striatum. However, in all other sites and with all other doses, cG-2allylP lessened the neural damage effects of hypoxia/ischemia. Moreover, cG-2allylP had an increased efficacy in brain regions that experienced progressive injury associated with delayed cell death, such as that associated with apoptosis. In brain regions such as the dentate gyrus and the cerebral cortex, that are more resistant to HI injury, the progression of injury is known to be slower and more severe than in the brain regions that are more sensitive to HI injury such as the striatum and the CA1-2, CA3 and CA4 subregions of the hippocampus. This result shows that cG-2allylP can be beneficial in treatment of chronic neurological disorders.

Example 8

Effects of cG-2-allylP on Pyridoxine-Induced Peripheral Neuropathy Pyridoxine Toxicity Model of Peripheral Neuropathy High doses of pyridoxine (vitamin B6) can produce neuropathy of peripheral sensory nerves in humans (Schaumburg et al., Sensory *Neuropathy from Pyridoxine Abuse. A New Megavitamin Syndrome*, New England J. Med. 309: 445-448 (1983), Albin et al., *Acute Sensory Neuropathy-from Pyridoxine Overdose*, Neurology 37: 1729-1732 (1987)). The observation provided a basis for development of a rat model of peripheral neuropathy (Windebank et al., *Pyridoxine neuropathy in rats: specific degeneration of sensory axons*, Neurology 35 (1985)).

Pyridoxine toxicity is characterized by the degeneration of sensory neurons, particularly the large axons of the proximal and distal peroneal and sural sensory nerves that descend from the sciatic nerve, resulting in reduced sensory fibre conduction velocity and functional incapacity (gait ataxia) in rats. Axonal degeneration is evidenced by an irregular-shaped profile of axons, with morphology characteristic of apoptosis, but not of demyelination (Perry et al., *Pyridoxine-Induced Toxicity in Rats: A Stereological Quantification of the Sensory Neuropathy*, Exp. Neurol. 190:133-144 (2004), incorporated herein fully by reference. In fact, the number of myelinated (small diameter) fibres increases following pyridoxine in inverse relation to the decrease in large A-cells.

The clinical relevance of these findings is not limited to vitamin overdose, but extends to neuropathies resulting from diabetes and the use of chemotherapeutic agents such as cisplatin and oxaliplatin, because those conditions are also characterized by large sensory fibre axonopathy (Schmeichel et al., *Oxidative Injury and Apoptosis of Dorsal Root Ganglion Neurons in Chronic Experimental Diabetic Neuropathy*, Diabetes 52: 165-171 (2003), Quasthoff and Hartung, *Chemotherapy-Induced Peripheral Neuropathy*, J. Neurol. 249:9-17 (2002)).

Perhiperal neuropathies can also be caused by glucose overdose, a condition that is closely related to diabetic neuropathy. Because similar cellular mechanisms underly pyridoxine-induced and diabetes-induced peripheral neuropathy (Table 1), studies of pyridoxine-induced peripheral neuropathy are reasonably predictive of diabetic peripheral neuropathy.

Materials and Methods

Pyridoxine was obtained from Sigma-Aldrich Chemical (St. Louis, Mo., USA) and cG-2-allylP was synthesized by the University of Auckland Department of Medicinal and Organic Chemistry (Auckland, New Zealand). All animal studies were approved by the Animal Ethics Committee of the University of Auckland and every effort was made to minimize animal suffering. Adult male Sprague-Dawley rats were used for the studies and were obtained from the Vernon-Jansen Unit, University of Auckland.

24 male Sprague-Dawley rats were habituated to walk across a wooden beam (4 cm diameter, 175 cm long, circular cross-section) over a training period of 8 days prior to initiating neuropathic toxicity treatment. Animals were weighed on the day prior to pyridoxine injection (mean body weight 270 g) and were randomized into treatment groups as follows: vehicle control (distilled water, n=16), 3 mg/kg cG-2-allylP (n=16) or 30 mg/kg cG-2-allylP (n=16). All groups received pyridoxine (400 mg/kg i.p.) 2/day for 8 days (days 1-8) and either vehicle or cG-2-allylP (3 or 30 mg/kg, p.o.) 1/day on days 1-10. Body weights were monitored throughout treatment and until study day 28. Beam walking was assessed on days 0 (baseline), 14, 21, and 28. Beam walk errors were assessed according to the method of Callizot (Callizot et al, *Pyridoxine-Induced Neuropathy in Rats: a Sensory neuropathy that Responds to 4-methylcatechol*, Neurobiol. Dis. 8:626-635 (2001.)) incorporated herein fully by reference. Each rat was scored for 7 steps taken in traversing the beam, as follows: 1=hind-paw placed on the top of the beam (normal); 2=paw contacted the lateral line of the beam; 3=paw overlapping the lateral line on the beam; 4=rat unable to place its feet on the beam. Rats that could walk across the beam therefore recorded a maximum functional deficit score of 28. Rats unable to take 7 steps along the beam scored 30, while rats unable to balance on the beam at all scored 32.

Statistical Analysis

Two-way analysis of variance (ANOVA) was conducted on beam walk performance data, with time and treatment as variables, applying Bonferroni post-hoc tests to assess individual treatment condition differences. Statistical significance was assumed if p<0.05.

Results

Effects of cG-2-allylP on Pyridoxine-Induced Weight Loss

In experimental animals, pyridoxine overdose causes the animals to slow their growth rates. Thus, animals do not gain weight as rapidly as animals not affected by the toxin. To determine if cG-2allylP affects this phenomenon, we studied a series of animals that received either pyridoxine alone, pyridoxine plus 3 mg/kg cG-2AllylP or pyridoxine plus 30 mg/kg cG-2allylP. Results of this study are shown in FIG. 5.

Figure 5:
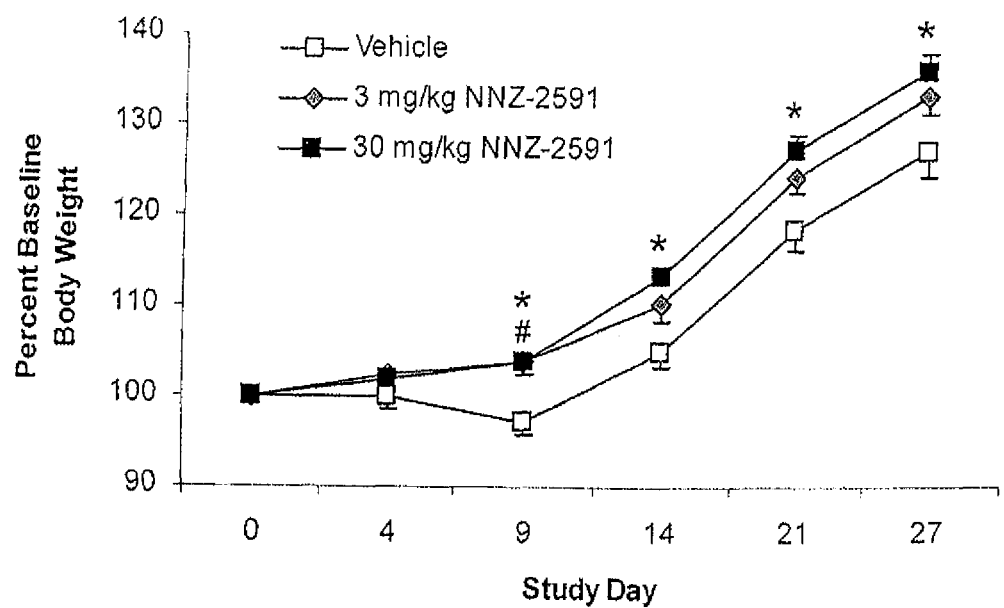
FIG. 5 shows body weight of rats expressed as percentage of baseline weight, following pyridoxine treatment (400 mg/kg, b.i.d., i.p., days 1-8) and either vehicle control (water) or cG-2-allylP (3 or 30 mg/kg, 1/day, p.o., days 1-10). #: $p<0.05$ vehicle compared to 3 mg/kg cG-2-allylP on the same test day; *: $p<0.05$ vehicle compared to 30 mg/kg cG-2-allylP on the same test day; Bonferroni post-hoc tests.

FIG. 5 shows body weight of rats expressed as percentage of baseline weight, following pyridoxine treatment (400 mg/kg, b.i.d., i.p., days 108) and either vehicle control (water) or cG-2allylP (3 or 30 mg/kg, 1/day, p.o., days 1-10). #: P<0.05 vehicle compared to 3 mg/kg cG-2allylP on the same test day; *: P<0.05 vehicle compared to 30 mg/kg cG-2allylP on the same test day; Bonferroni post-hoc tests.

Oral cG-2allylP treatment at a dose of either 3 mg/kg or 30 mg/kg, 1/day for 10 days to pyridoxine-intoxicated rats resulted in greater gain of body weight than in animals treated with pyridoxine alone (vehicle controls) (FIG. 5).

Although cG-allylP was effective at a dose of 3 mg/kg, it was more effective when administered at a dose of 30 mg/kg (FIG. 5). ANOVA revealed that the effect of treatment on body weight was statistically significant ($F_{2,225}$=5.48; p<0.01). Bonferroni post-hoc tests demonstrated that 3 mg/kg cG-2-allylP significantly attenuated the effect of pyridoxine on body weight on test day 9 (p<0.05), while 30 mg/kg cG-2-allylP was observed to significantly attenuate pyridoxine-mediated body weight loss on days 9, 14, 21 and 28 (p<0.05).

Effects of cG-2-allylP on Pyridoxine-Induced Locomotor Dysfunction

Figure 6:
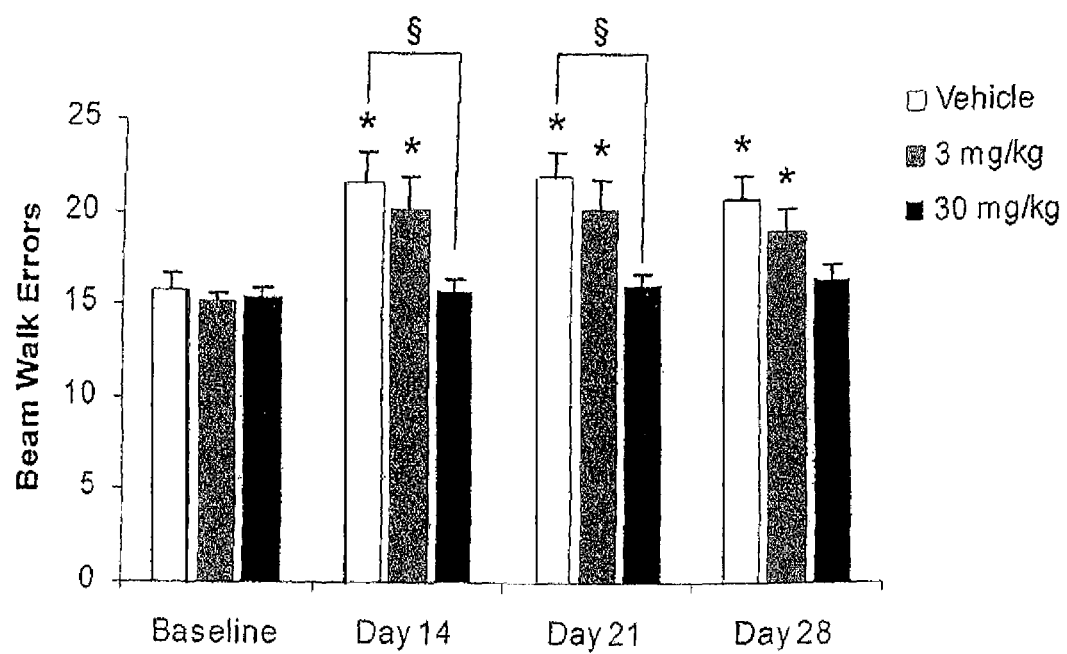
FIG. 6 shows beam walk error scores for rats receiving pyridoxine treatment (400 mg/kg, b.i.d., i.p., days 1-8) and either vehicle control (water) or cG-2-allylP treatment (3 or 30 mg/kg, 1/day, p.o., days 1-10). Scores represent the aggregate severity score for 7 steps, with each step scored between 1 (normal) and 4 (maximum fault). *: $p<0.01$ compared to baseline score for the same treatment group; §: $p<0.05$ compared to vehicle on the same test day; Bonferroni post-hoc tests.

Treatment of rats with pyridoxine (400 mg/kg, b.i.d., i.p., 8 days) produced a significant increase in beam walking errors (significant effect of treatment by ANOVA, $F_{2,135}$=5.03, p=0.01), with the increase observed as statistically significant on each day tested (days 14, 21 and 28; Bonferroni post-hoc tests, p<0.01 compared to vehicle-treated animals at baseline) (FIG. 6).

Treatment with cG-2-allylP (30 mg/kg, p.o., days 1-10) effectively prevented pyridoxine-induced beam walking errors. This effect was consistently observed on each test day (Bonferroni post-hoc tests, p<0.05; FIG. 6) compared to animals treated with vehicle alone.

Conclusions

The mechanism by which pyridoxine induces an axonopathy of descending sensory nerves is not completely understood. The lack of a competent nerve-blood barrier at the site of the dorsal root ganglia may underlie the apparent sensitivity of peripheral sensory nerves to pyridoxine over motor neurons and the CNS (H. Schaumburg, J. Kaplan, A. Windebank, N. Vick, S. Rasmus, D. Pleasure, M. J. Brown, *Sensory neuropathy from pyridoxine abuse. A new megavitamin syndrome*, N. Engl. J. Med. 309 (1983); Perry et al., *Pyridoxine-induced toxicity in rats: a stereological quantification of the sensory neuropathy*, Exp Neurol. 190 (2004)). It has been postulated that pyridoxine alters neuronal metabolism such that the neurons cannot support axonal energy needs, resulting in a reversible degeneration (Windebank et al., *Pyridoxine neuropathy in rats: specific degeneration of sensory axons*, Neurology 35 (1985); Krinke et al., *Pyridoxine megavitaminosis: an analysis of the early changes induced with massive doses of vitamin B6 in rat primary sensory neurons*, J Neuropathol. Exp. Neurol. 44 (1985)), however the specific biochemical basis for this metabolic dysfunction is not entirely clear.

Regardless of the mechanism(s) underlying pyridoxine toxicity, cG-2-allylP can inhibit sensory axon degeneration in the rat. Axonal degeneration in the rat is evidenced by an irregular-shaped profile of axons, with morphology characteristic of apoptosis, but not of demyelination (Perry et al., *Pyridoxine-induced toxicity in rats: a stereological quantification of the sensory neuropathy*, Exp Neurol. 190 (2004)). In fact, the number of myelinated (small diameter) fibres increases following pyridoxine in inverse relation to the decrease in large A-cells. We believe that cG-2-allylP was effective in the current study through inhibition of apoptosis of these large sensory neurons.

Previously, studies carried out in rats exposed to hypoxia/ischaemia found that cG-2-allylP decreased expression of cleaved caspase-3 protein in the cerebral cortex (Guan et al, *Peripheral Administration of a Novel Diketopiperazine, NNZ-2591, Prevents Brain Injury and Improves Somatosensory-Motor Function Following Hypoxia-Ischemia in Adult Rats*, Neuropharmacology 53:749-762 (2007)). Caspase-3 is a key mediator in the apoptotic cascade of neurons, suggesting that cG-2-allylP reduces neuronal degeneration through interruption of apoptosis. Apoptosis is understood to be a key mechanism in the development of neuropathy in diabetes, with even short-term hyperglycemia resulting in neuronal apoptosis (Vincent et al., *Short-Term Hyperglycemia Produces Oxidative Damage and Apoptosis in Neurons*, FASEB J 19:638-640 (2005)). Hyperglycemia can be promoted by the upregulation of the pro-apoptotic protein Bax (Sharifi et al., *Study of high glucose-induced apoptosis in PCI 2 cells: role of bax protein*, J. Pharmacol. Sci. 104 (2007)). While hyperglycemia is peculiar to diabetes, these reports support the conclusion that an anti-apoptotic drug that shows efficacy in the pyridoxine neuropathy model can also be of utility in diabetic neuropathy.

cG-2-allylP has also been reported to reduce activation of microglia in response to hypoxia-ischemia in rat model (Guan et al., Neuropharmacology 53:749-762 (2007)). Recently, an association between microglial activation and development and persistence of neuropathic pain has been disclosed (Ji et al., p38 *MAPK, Microglia Signalling and Neuropathic Pain*, Mol Pain, 3:33-41 (2007). In conditions of neuronal stress, the microglia associated with neurons can activate mitogen-activated protein kinase (MAPK) p38 to promote the inflammatory response (Id.) The activation of these microglia appears to require ligand activation of P2Y12 receptors (Tozaki-Saitho et al., *P2Y12 Receptors in Spinal Microglia are Required for Neuropathic Pain After Peripheral Nerve Injury*, J. Neurosci, 28:4949-4956 (2008)). Such activation is reported to be prevented by antagonism of microglia-bound toll-like receptor 4 (TLLR4) (Bettoni et al, *Glial TLR4 Receptor as New Target to Treat Neuropathic Pain: Efficacy of a New Receptor antagonist in a Model of Peripheral Nerve Injury in Mice*, Glia 56:1312-1319 (2008)). A molecule that depresses microglia activation, such as cG-2-allylP, in the present example has also shown efficacy against neuropathic pain as well as somatosensory dysfunction.

Example 9

High Dose Tolerance to cG-2-allylP

In this example, male Sprague Dawley rats were administered either 150 mg/kg or 500 mg/kg cG-2-allylP (p.o.; n=5/dose) or vehicle control (p.o.; n=4) and observed for clinical signs indicative of central or systemic toxicity or secondary pharmacology, according to a modified Irwin neurobehavioral observation test (Irwin, S. *Comprehensive observational assessment: 1a. A Systematic, Quantitative Procedure for Assessing the Behavioral and Physiologic State of the Mouse*, Psychopharmacologia 13:222-257 (1968)), incorporated herein fully by reference. Observations were made just prior to administering (baseline) and then at 15 min, 1, 2, 4 and 24 h following treatment. Clinical signs were scored using a 0-4 scale for the appearance and severity of sedation and hyperactivity, stereotypic behaviours, respiration rate, tremors, twitches and convulsions, pelvic elevation, tail elevation, abnormalities of gait, piloerection, toe-pinch responsivity, abdominal tone (palpation of abdomen), pupil size, diarrhoea and salivation.

Results

High doses of cG-2-allylP (150 mg/kg and 500 mg/kg; n=5 per group) had no observable effect on rat behaviour or physiology compared to vehicle-treated animals (n=4) as determined by the modified Irwin screen. All animals recorded a score indicative of normality for all measures at both drug doses administered.

Example 10

Effects of cG-2allylP on Streptozotocin Induced Diabetic Neuropathy

Introduction

Streptozotocin is known to cause degeneration and loss of function of pancreatic cells resulting in decreased insulin production, thereby leading to diabetes, which results in hyperglycemia of the affected animals. Many studies have shown parallels between streptozotocin-induced diabetes and diabetes in human beings (see Table 1). Therefore, studies of effects of agents on streptozotocin-induced diabetic conditions in animals are reasonably predictive of effects to be observed in human beings with diabetes.

Methods

Rats (225-250 g) are rendered diabetic by an i.p. injection of streptozotocin (STZ; 75 mg/kg). A diabetic condition is confirmed in each rat 10 days later by measurement of tail vein blood glucose levels. Only rats with a final blood glucose level>13.8 mM are considered diabetic and are included in the experiment.

Hyperglycemic, diabetic rats are dosed with cG-2-allylP (3-30 mg/kg, p.o. 1/day) from day 14 until day 28 (for a total of 14 days of treatment). Glucose measurements are taken on day 14 (pre-dose), day 21, day 28 and day 42.

Rats are tested for tactile allodynia on days 14 (pre-dose), and on days 16, 21, 28, 35 and 42 using van Frey hairs. Rats are tested for responsivity to von Frey hairs with calibrated bending forces of 1.5-15 g, to deliver punctate mechanical stimuli of varying intensities. Filaments exerting a force above 15 g are not used. Starting with the lowest filament force (1.5 g), von Frey hairs are applied to the plantar surface of the hind paw, with sufficient force to cause slight bending against the paw, and held for 1 s. Each stimulation is applied five times with an inter-stimulus interval of 5-10 s. Care is taken to stimulate random locations on the plantar surface. A positive response is noted if the paw was robustly and immediately withdrawn. Paw-withdrawal threshold is defined as the minimal pressure required to elicit a withdrawal reflex of the paw, at least one time from the five trials. Voluntary movement associated with locomotion is not considered a withdrawal response. If no response is noted in any trial, the process is repeated with the following force hair, and the filament that produces a positive response is noted as the threshold.

Results

Daily oral cG-2-allylP treatment to diabetic rats for a period of 14 days is observed to increase the pain threshold in response to von Frey hair pressure to the plantar surface of the hind paws. Therefore, cG-2allylP is effective in treating streptozotocin-induced diabetic peripheral neuropathy. Because streptozotocin-induced diabetic peripheral neuropathy is reasonably predictive of diabetic peripheral neuropathy in human beings, this example supports the use of cG-2allylP in the treatment of human beings with diabetic peripheral neuropathy.

The above descriptions and examples demonstrate that cG-2-allylP can be an effective treatment for a variety of clinically significant conditions, including both those of the central and peripheral nervous systems. Further, we have demonstrated that cG-2-allylP can be effectively delivered via subcutaneous or oral routes, and that when administered, cG-2-allylP has desirable pharmacokinetic properties, making it a useful agent for in vivo therapy of disorders of the central and peripheral nervous systems of non-human animals and human beings. Because of the substantial parallels in cellular pathologies in pyridoxine-induced peripheral neuropathy, neuropathies caused by toxins (eg, cisplatin and hyperglycemia) and found in diabetics, cG-allylP can be effectively used to treat a variety of peripheral neuropathies in human beings.

The descriptions and examples provided herein are for purposes of illustration only. The scope of this invention to is not intended to be limited to the described embodiments. Other embodiments incorporating elements of the invention can be practiced without undue experimentation by persons of ordinary skill in the art. All such embodiments are therefore considered to be part of this invention. All references cited herein are incorporated fully by reference.

What is claimed is:

1. A method for treating a peripheral neuropathy caused by diabetes or pyridoxine in a mammal in need thereof, comprising: administering to said mammal a pharmaceutically effective amount of the compound having the formula:

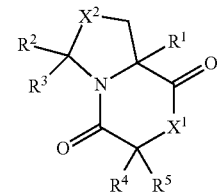

or a pharmaceutically acceptable salt or hydrate thereof, wherein $R^1$=allyl, $R^2$=$R^3$=$R^4$=$R^5$=H, $X^1$=NH, $X^2$=$CH_2$, said compound being cyclic Glycyl-2-allylProline (cG-2-allylP)).

2. The method of claim 1, wherein said compound is administered in an aqueous solution and one or more pharmaceutically acceptable excipients, additives, carriers or adjuvants.

3. The method of claim 1, wherein said method further comprises administering the compound in a composition comprising one or more excipients, carriers, additives, adjuvants or binders in a tablet or capsule.

4. The method of claim 1, wherein said cG-2-allylP is administered orally.

5. The method of claim 1, wherein said cG-2-allylP is administered via a route selected from the group of oral, intraperitoneal, intravascular, peripheral circulation, subcutaneous, intraorbital, ophthalmic, intraspinal, intracisternal, topical, infusion, implant, aerosol, inhalation, scarification, intraperitoneal, intracapsular, intramuscular, intranasal, buccal, transdermal, pulmonary, rectal, and vaginal.

6. The method of claim 1, wherein the amount of said compound has a lower limit of about 0.01 milligrams per kilogram mass of the mammal per day (mg/kg/day) and an upper limit of about 100 mg/kg/day.

7. The method of claim 1, wherein said amount has a lower limit of about 3 mg/kg/day and an upper limit of about 30 mg/kg/day.

8. The method of claim 1, wherein said peripheral neuropathy is a toxic neuropathy caused by pyridoxine.

9. The method of claim 1, wherein said peripheral neuropathy is diabetic peripheral neuropathy.

* * * * *